United States Patent [19]

Wadsworth et al.

[11] Patent Number: 5,217,975
[45] Date of Patent: Jun. 8, 1993

[54] AZABICYCLIC COMPOUNDS FOR TREATING DEMENTIA

[75] Inventors: Harry J. Wadsworth; Sarah M. Jenkins, both of Essex, England

[73] Assignee: Beecham Group p.l.c., Brentford, England

[21] Appl. No.: 532,937

[22] Filed: Jun. 4, 1990

[30] Foreign Application Priority Data

Jun. 6, 1989 [GB] United Kingdom ............ 8912991
Dec. 18, 1989 [GB] United Kingdom ............ 8928554

[51] Int. Cl.$^5$ .................. C07D 211/04; A61K 31/44
[52] U.S. Cl. ................................ 514/299; 514/305; 546/112; 546/133
[58] Field of Search ............. 546/112, 133; 514/299, 514/305

[56] References Cited

FOREIGN PATENT DOCUMENTS

| | | |
|---|---|---|
| 0261763 | 3/1988 | European Pat. Off. |
| 0287356 | 10/1988 | European Pat. Off. |
| 0296721 | 12/1988 | European Pat. Off. |
| 0363085 | 4/1990 | European Pat. Off. |
| 0366304 | 5/1990 | European Pat. Off. |

*Primary Examiner*—Marianne M. Cintins
*Assistant Examiner*—Catherine S. Kilby Scalzo
*Attorney, Agent, or Firm*—Hopgood, Calimafde, Kalil, Blaustein & Judlowe

[57] ABSTRACT

A compound of formula (I) useful for treating dementia or a pharmaceutically acceptable salt thereof:

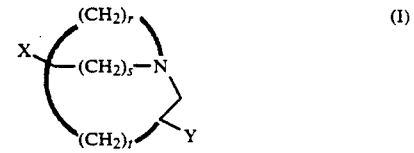

in which one of X and Y represents hydrogen and the other represents Z, where Z is a group

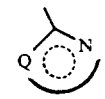

in which Q represents a 3-membered divalent residue completing a 5-membered aromatic ring and comprises two or three nitrogen atoms, any amino nitrogen being substituted by a $C_{1-2}$ alkyl, cyclopropyl or propargyl group, r represents the integer of 2 or 3, s represents an integer of 1 or 2 and t represents 0, with the proviso that when Y is hydrogen s is 1.

9 Claims, No Drawings

AZABICYCLIC COMPOUNDS FOR TREATING DEMENTIA

This invention relates to compounds having pharmaceutical activity, to a process for their preparation and their use as pharmaceuticals.

EP-A-0261763 and EP-A-0287356 disclose certain non-aromatic 1-azabicyclic ring systems substituted at the 3-position by certain 5-membered aromatic heterocycles.

A novel group of compounds has now been discovered which enhance acetylcholine function via an action at muscarinic receptors within the central nervous system and are therefore of potential use in the treatment and/or prophylaxis of dementia in mammals.

According to the present invention, there is provided a compound of formula (I) or a pharmaceutically acceptable salt thereof:

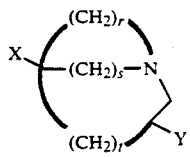

(I)

in which one of X and Y represents hydrogen and the other represents Z, where Z is a group

in which Q represents a 3-membered divalent residue completing a 5-membered aromatic ring and comprises two or three nitrogen atoms, any amino nitrogen being substituted by a $C_{1-2}$ alkyl, cyclopropyl or propargyl group, r represents an integer of 2 or 3, s represents an integer of 1 or 2 and t represents 0 or 1, with the proviso that when Y is hydrogen s is 1.

Certain compounds of formula (I) are capable of existing in a number of stereoisomeric forms including enantiomers. The invention extends to each of these stereoisomeric forms, and to mixtures thereof (including racemates). The different stereoisomeric forms may be separated one from the other by the usual methods, or any given isomer may be obtained by stereospecific or asymmetric synthesis.

In compounds of formula (I) having two assymmetric centres where Y is other than hydrogen, the stereochemical configuration in which the group Y and the $(CH_2)s$ bridge are on the same side of the plane of the molecule which contains both bridgehead atoms and the ring carbon atom bonded to the group Y will herein be referred to as the exo configuration. Similarly, the configuration of compounds in which the group Y and the bridge $(CH_2)s$ are on opposite sides of the above-mentioned plane of the molecule will herein be referred to as the endo configuration. Preferably compounds of formula (I) have the exo configuration.

The compounds of formula (I) can form acid addition salts with acids, such as the conventional pharmaceutically acceptable acids, for example hydrochloric, hydrobromic, phosphoric, acetic, fumaric, salicylic, citric, lactic, mandelic, tartaric, oxalic and methanesulphonic.

Preferred combinations of (r, s, t) include (2,2,0), (3,1,0), (2,1,0), (2,1,1) and (3,1,1). Examples of combinations of (r, s, t) include (2,1,0), (3,1,0) and (2,2,0).

5-Membered aromatic heterocycles within the definition of variable Z include 1-alkyl-1,2,3-triazol-4-yl, 2-alkyl-1,2,3-triazol-4-yl, 3-alkyl-1,2,3-triazol-4-yl, 1-alkyl-1,2,4-triazol-3-yl, 1-alkyltetrazol-5-yl and 2alkyltetrazol-5-yl, in which 'alkyl' signifies a $C_{1-2}$ alkyl, cyclopropyl or propargyl group. The alkyl substituent on Z is preferably at the 2-position of 1,2,3-triazol-4-yl and tetrazol-5-yl and at the 1-position of 1,2,4-triazol-3-yl. A preferred substituent on the amino nitrogen of group Z is methyl. Examples of Z include 1-methyl-1,2,3-triazol-4-yl, 2-methyl-1,2,3-triazol-4-yl, 3-methyl-1,2,3-triazol-4-yl, 2-ethyl-1,2,3-triazol-4-yl, 1-methyl-1,2,4-triazol-3-yl, 1-methyltetrazol-5-yl, 2-methyltetrazol-5-yl and 2-ethyltetrazol-5-yl. The invention also provides a process for the preparation of a compound of formula (I), or a pharmaceutically acceptable salt thereof, which process, which process comprises:

(a) cyclising a compound of formula (II):

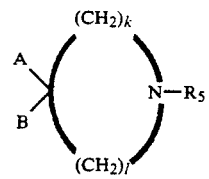

(II)

in which (i) A represents Z or a group convertible thereto and B represents $—(CH_2)_jL_1$ where $L_1$ is a leaving group or A and $L_1$ together represent $—COO—$; one of j, k and l is 1 and the other two independently represent an integer of 2 or 3, and $R_5$ represents hydrogen or an N-protecting group; to give a compound of formula (IIa):

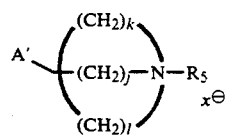

(IIa)

in which A' represents Z or a group convertible thereto, $x^-$ is an anion and the remaining variables are as previously defined;

or (ii) A represents an electron withdrawing group, B represents hydrogen and $R_5$ represents $—(CH_2)_j L_2$ where $L_2$ is a leaving group; one of k and l is 1 and the other and j independently represent an integer of 2 or 3; to give a compound of formula (IIb):

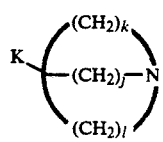

(IIb)

in which K represents an electron withdrawing group or A' and the remaining variables are as previously defined; and thereafter, optionally or as necessary and in any appropriate order, removing any $R_5$ N-protecting group, converting K to A', converting A' to Z, optionally interconverting Z and/or forming a pharmaceutically acceptable salt; or (b) cyclising a compound of formula (III):

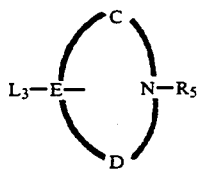

(III)

where $R_5$ is hydrogen or an N-protecting group, and either C is one, D is another and E is the remainder of $-(CH_2)_r-$, $-(CH_2)_s-$ and $-(CH_2)_r-CHA'-CH_2-$ or groups convertible thereto, A' is Z or a group convertible thereto and $L_3$ is a leaving group; or C is one and E is the other of $-(CH_2)_r-$ and $-(CH_2)_s-$ or groups convertible thereto and D represents $-(CH_2)_r-CHA'-CH_2-$ where A' and $L_3$ together represent $-COO-$, and thereafter, optionally or as necessary and in any appropriate order, converting C, D and E to $-(CH_2)_r-$, $-(CH_2)_s-$ and $-(CH_2)_r-CHA'-CH_2-$, removing any $R_5$ protecting group, converting A' to Z, optionally interconverting Z and/or forming a pharmaceutically acceptable salt; or (c) cyclising a compound of formula (IV):

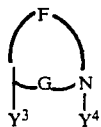

(IV)

where F is one and G is the other of $-(CH_2)_r-$ and $-(CH_2)_s-$ or groups convertible thereto, and one of $Y^3$ and $Y^4$ is $-(CH_2)_u-K$ and the other is $-(CH_2)_v W$ or $-(CH_2)_v L_4$ where K and W are electron withdrawing groups, $L_4$ is a leaving group, u is 1 or 2 and v is 0 or 1, with the provisos that, when $Y_4$ is $-(CH_2)_v W$, v is 1, and $Y_4$ is not $-(CH_2)_v L_4$, and thereafter, optionally or as necessary and in any appropriate order, hydrolysing and decarboxylating the cyclisation product and converting the carbonyl group to CHA' where A' is Z or a group convertible thereto, converting K to A' as defined, converting A' to Z, converting F and G to $-(CH_2)_r-$ and $-(CH_2)_s-$ as appropriate, interconverting Z and/or forming a pharmaceutically acceptable salt, u and v being such that the desired compound of formula (I) is obtained.

It will be appreciated that the product of process variant (a) is a compound of formula (I) in which variable Y is hydrogen and that the product of process variant (b) or (c) is a compound of formula (I) in which variable X is hydrogen.

In process variant (a), examples of the leaving groups $L_1$ and $L_2$ include halo such as chloro or bromo, tosyloxy and mesyloxy.

Examples of $R_5$ when an N-protecting group include benzyl and substituted benzyl.

Examples of A and A' include alkoxycarbonyl, benzyloxycarbonyl and cyano.

The cyclisation reaction is a nucleophilic substitution which may be carried out under conventional conditions appropriate to the groups A and B. Thus, when B is $(CH_2)_j Br$ and A is $C_{1-4}$ alkoxycarbonyl, the cyclisation is carried out in an inert solvent such as toluene or ether at elevated temperature. When B is $(CH_2)_j OTos$ or $(CH_2)_j O-Mes$, it is preferably obtained by treatment of a $(CH_2)_j OH$ group with a suitable reagent such as tosylchloride or mesyl chloride, in a base such as pyridine, whereupon the cyclisation may proceed at ambient temperature, or at elevated temperature in an inert solvent such as toluene. When A and $L_1$ together represent $-COO-$, the cyclisation may be carried out in a lower alkanol such as ethanol in the presence of acid such as hydrogen bromide followed by treatment with base such as aqueous potassium carbonate. In the resulting compound of formula (IIa), A' will be an alkoxycarbonyl group corresponding to the lower alkanol used for the cyclisation.

Where $R_5$ is an N-protecting group such as benzyl, this may be removed by conventional hydrogenation, preferably catalytically over a suitable catalyst such as Pd/C. Where A' or K is benzyloxycarbonyl, deesterification and deprotection may be effected simultaneously by conventional hydrogenation.

Examples of A when an electron withdrawing group include $C_{1-4}$ alkoxycarbonyl and cyano.

When A is an electron withdrawing group such as $C_{1-4}$ alkoxycarbonyl, B is hydrogen and $R_5$ is $-(CH_2)_j L_2$ where $L_2$ is, for example, chloro, the cyclisation may be effected by treatment of the compound of formula (II) with lithium diisopropylamide in a suitable solvent such as ether.

In process variant (b), examples of leaving groups $L_3$ include halo such as chloro and hydroxy. In process variant (c), examples of $L_4$ include those given for $L_3$ or $C_{1-4}$ alkoxy such as ethoxy. Examples of electron withdrawing groups K and W include $C_{1-4}$ alkoxycarbonyl and cyano. In the group $-(CH_2)_r-CHA'-CH_2-$, examples of A' include hydroxy, cyano and formyl.

In process variant (b), where $L_3$ is hydroxy and D is $-(CH_2)_r-CHOH-CH_2-$, the cyclisation of compounds of formula (III) may be carried out by pyrolysis, by the method of D. O. Spry and H. S. Aaron, J. Org. Chem., 1969, 34, 3674, to yield a compound where A' is hydroxy.

Where E is $-(CH_2)_r-CO-CH_2-$, the cyclisation may be carried out under basic conditions where $R_5$ is benzyl (F. I. Carrol, A. M. Ferguson, and J. B. Lewis, J. Org. Chem. 31, 2957, 1966). The resulting ketone may be reacted with tosylmethyl isocyanide to yield a compound where A' is cyano, or with methoxymethyl triphenyl phosphonium chloride and potassium t-butoxide in dimethyl formamide followed by aqueous acid hydrolysis of the enol ether to yield a compound where A' is formyl.

Where $L_3$ and A' together represent $-COO-$, the cyclisation is a rearrangement reaction which can be carried out under acid conditions in a polar solvent, preferably hydrogen bromide in ethanol, at ambient temperature followed by treatment with base such as aqueous potassium carbonate, to yield a compound where A' is a carboxy ester group. It is preferred to protect the nitrogen atom with an $R_5$ N-protecting group such as benzyl, which may be subsequently removed by hydrogenation over a suitable catalyst such as Pd/C.

In process variant (c), where $Y^3$ and $Y^4$ both contain carboxy ester groups the cyclisation of compounds of formula (IV) is a Dieckmann reaction which is catalysed by a base such as potassium t-butoxide at elevated temperature in a solvent such as toluene.

The resulting β-keto ester is hydrolysed and decarboxylated under conventional conditions such as heating at reflux in dilute hydrochloric acid.

The carbonyl group may be reduced to an A' hydroxy group with a suitable reducing agent such as sodium borohydride in ethanol at ambient temperature, or sodium in ethanol at elevated temperature, such as the boiling point of the solvent, under an inert atmosphere such as nitrogen, depending on the stereochemistry required.

An A' hydroxy group may be converted to cyano by first converting it to a good leaving group such as mesyloxy or tosyloxy and then displacing it with cyanide ion. Alternatively, the carbonyl group may be converted directly to an A' cyano group or a formyl group as described above under process variant (b). In process variant (c) where $Y_3$ and $Y_4$ both contain cyano groups the cyclisation is a Thorpe reaction which is catalysed by a base such as potassium t-butoxide at elevated temperature in a solvent such as toluene.

The resulting β-keto nitrile is hydrolysed and decarboxylated under conventional conditions such as heating at reflux in dilute hydrochloric acid.

Where $Y^3$ is —$(CH_2)_vL_4$, the cyclisation may be carried out as described in EP-0094742 under basic conditions such as sodium hydride and potassium t-butoxide, in an inert polar solvent such as dimethylformamide.

Conversions of groups A' and K, and interconversions of Z, may be carried out conventionally, see for example standard text books on heterocyclic chemistry such as 'Comprehensive Heterocyclic Chemistry', A. R. Katritzky and C. W. Rees, Pergamon, 1984.

The A' or K group is first converted, as necessary, to a suitable starting group Z' for the chosen conversion reaction to give the required group Z.

A Z' formyl group may be obtained by conventional reduction of an A' alkoxycarbonyl group with a reducing agent such as diisobutylaluminium hydride or, more preferably hydrolysis with acid, followed by conversion to the acid chloride by treatment with thionyl chloride at elevated temperature to yield a Z' chlorocarbonyl group and reaction with O-N-methylated dimethyl hydroxylamine hydrochloride in the presence of pyridine in a suitable solvent such as dichloromethane to give the O-N-dimethyl hydroxamic acid. Reduction with diisobutyl aluminium hydride yields the required formyl group.

A Z' acetyl group may be obtained by treatment of the abovementioned O-N-dimethyl hydroxamic acid with methyl lithium.

An A' hydroxy group may be oxidised to a carbonyl group by treatment with chromic acid or using dimethyl sulphoxide and dicyclohexylcarbodiimide, and the carbonyl group converted to cyano or formyl as described above under process variant (b).

A Z' aminocarbonyl group may be obtained by treatment of a Z' chlorocarbonyl group with ammonia, and a Z' cyano group may be obtained by treatment of the Z' aminocarbonyl group with a dehydrating agent such as phosphorus pentoxide in toluene or trifluoroacetic anhydride in tetrahydrofuran.

When Z represents a 1,2,3-triazol-4-yl group, a Z' formyl group may be treated with triphenyl phosphine, carbon tetrabromide and zinc in an inert solvent such as dichloromethane at ambient temperature to provide a 2,2-dibromoethenyl group which may be eliminated with n-butyl lithium in hexane to give an ethynyl group.

Treatment of the latter with azidotrimethyl silane in an inert solvent such as tetrahydrofuran at elevated temperature followed by lower alcohol at ambient temperature yields the unsubstituted 1,2,3-triazol-4-yl group which is alkylated as required. A 2-alkyl group may be introduced by treatment with the corresponding diazoalkane in ether at ambient temperature.

Alternatively a Z' acetyl group may be successively treated with hydrogen chloride, chlorine and triphenylphosphine to yield a triphenylphosphinemethylenecarbonyl group which may be treated with m-nitrobenzoyl azide in acetonitrile at elevated temperature to yield the 1,2,3-triazol-4-yl group which is protected at the 1 position by m-nitrobenzoyl. The protecting group may be removed by prolonged heating in a lower alcohol, by treatment with ammonia or by chromatography on basic alumina in a lower alcohol. The resulting unsubstituted 1,2,3-triazol-4-yl group may then be alkylated as described above.

Compounds of formula (I) in which Z represents a 1-alkyl or 3-alkyl-1,2,3-triazol-4-yl group may be obtained as minor products in the preparation of the corresponding 2-alkyl-1,2,3-triazol-4-yl compounds and separated chromatographically.

When Z represents a 2-alkyltetrazol-5-yl group, a Z' cyano group may be treated with azidotrimethyl silane in an inert solvent such as tetrahydrofuran or dioxan at elevated temperature to yield a trimethylsilyl-substituted tetrazol-5-yl group. Treatment of the latter with a lower alcohol such as methanol effects deprotection of the amino nitrogen which may then be alkylated as described above.

Compounds of formula (I) in which Z represents a 1-alkyltetrazol-5-yl group may be obtained as a minor product in the preparation of the corresponding 2-alkyltetrazol-5-yl compound and separated chromatographically.

When Z represents a 1,2,4-triazol-3-yl group a Z' cyano group may be treated with dry ethanol saturated with hydrogen chloride gas to give an imidate. This may be treated with an alkyl hydrazine to form the corresponding amidrazone. Treatment of this with anhydrous formic acid or triethyl orthoformate will give the required 1-alkyl-1,2,4-triazol-3-yl group.

Where applicable, an endo isomer may be obtained by epimerisation of a corresponding exo isomer or vice versa, the epimerisation reaction being effected by standard procedures at any convenient stage in the process but preferably before the introduction of the group Y. (Saunders et al., J. Chem. Soc. Chem. Comm. 1988 p 1618).

In a further aspect the invention provides a process for the preparation of a compound of formula (I), or a pharmaceutically acceptable salt thereof, which process comprises reacting a compound of formula (IVa):

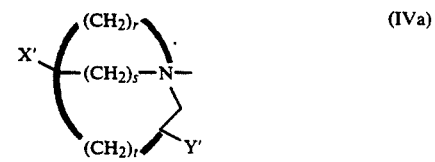
(IVa)

in which r,s and t are as defined in formula (I), one of X' and Y' represents hydrogen and the other represents Z' wherein Z' is a group convertible to Z as defined in formula (I), to convert Z' to Z and thereafter optionally forming a pharmaceutically acceptable salt.

Compounds of formula (II) may be prepared conventionally.

Where A is $C_{1-4}$ alkoxycarbonyl, B is $(CH_2)_jL_1$ and $R_5$ is hydrogen or an N-protecting group, the compound of formula (II) may be prepared by treating a compound of formula (V):

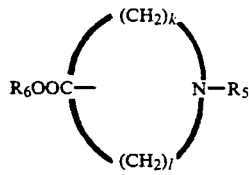

where $R_6$ is $C_{1-4}$ alkyl and the remaining variables are as previously defined, with lithium diisopropylamide, prepared in situ from diisopropylamine and n-butyllithium followed by reaction with a compound $L_5(CH_2)_jL_1$ where $L_5$ is a leaving group, in an inert solvent such as ether at depressed to elevated temperature. Both $L_1$ and $L_5$ are suitably bromo.

Where A and $L_1$ together represent —COO— and j is 2, the compound of formula (II) may be prepared by reacting the compound of formula (V), treated with lithium diisopropylamide as before, with ethylene oxide in an inert solvent such as ether at depressed to elevated temperature.

Alternatively, the compound of formula (II) where A and $L_1$ together represent —COO, k is 2 and l is 1 may be prepared by a 1,3-dipolar cycloaddition reaction which involves reacting a compound of formula (VI):

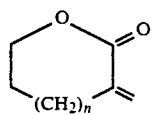

where n is 0 or 1, with a compound of formula (VII):

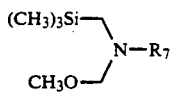

in which $R_7$ is an N-protecting group, in the presence of a catalytic amount of trifluoroacetic acid.

Where A is an electron withdrawing group such as $C_{1-4}$ alkoxycarbonyl, B is hydrogen and $R_5$ is $(CH_2)_jL_2$, the compound of formula (II) may be prepared by reacting the compound of formula (V) where $R_5$ is hydrogen with a compound $L_5(CH_2)_jL_2$ where $L_5$ is as previously defined, in a solvent such as acetone in the presence of a base such as potassium carbonate. The leaving group $L_5$ is preferably bromo and $L_2$ is preferably chloro.

Compounds of formulae (V) are known compounds or may be prepared by analogous methods to those for preparing known compounds. The compound of formula (V) where k is 2, l is 1 and $R_5$ is benzyl may be prepared by the cyclisation of di-$C_{1-4}$ alkyl itaconate in the appropriate alkanol with benzylamine at elevated temperature, followed by reduction of the resulting oxo group at the 2-position of the pyrrolidine ring with $BH_3$ in tetrahydrofuran, at ambient to elevated temperature.

Alternatively, and preferably, a dipolar cycloaddition of a $C_{1-4}$ alkyl acrylate with a compound of formula (VII) in the presence of a catalytic amount of trifluoroacetic acid yields a compound of formula (V) directly.

Intermediates of formulae (III) and (IV) are known compounds (e.g. as described in EP-A-0094742) or may be prepared analogously.

Intermediates of formula (III) where A and $L_3$ together represent —COO—, t=0, C is —$(CH_2)_2$— and E is —$CH_2$— are described in, for example, Kuthan et al., Coll. Czechoslov. Chem. Comm., 1977, 42, 283 or may be prepared therefrom by conventional hydrogenation of the pyridine ring over 5% Pt/C, and benzylation of the nitrogen atom by treatment with benzyl bromide and potassium carbonate in dry acetone.

The compound of formula (III) where A' and $L_3$ together represent —COO—, t=0, C is —$CH_2$— and E is —$(CH_2)2$ may be prepared by a 1,3-dipolar cycloaddition reaction of a compound of formula (VII) with 5,6-dihydro-2H-pyran-2-one in the presence of a catalytic amount of trifluoroacetic acid.

Intermediates of formula (III) where $L_3$ is a leaving group are described in, for example, Spry et al., J. Org. Chem., 1969, 34, 3674 and Hasse et al., Chem. Ber., 1960, 93, 1686.

Intermediates of formula (IV) are described in or may be prepared from intermediates of formula (V) as described in, for example, Martell et al., J. Pharm. Sci., 1963, 52(4), 331, Sternbach et al., J.A.C.S., 1952, 74, 2215, Thill et al., J. Org. Chem., 1968, 33, 4376 and EP-0 094 742.

Compounds of formulae (VI) and (VII) may be prepared conventionally. Thus, a compound of formula (VI) may be obtained by the reaction of γ-butyrolactone with ethyl formate in the presence of base such as sodium hydride followed by reaction of the resulting formyl derivative (as the enol salt) with formaldehyde. A compound of formula (VII) may be obtained by the reaction of the primary amine $R_7NH_2$ successively with chloromethyltrimethylsilane and formaldehyde followed by methanol and anhydrous potassium carbonate.

Pharmaceutically acceptable salts of the compounds of formula (I) may be formed conventionally by reaction with the appropriate acid such as described above under formula (I).

The invention also provides novel intermediates of formula (VIII):

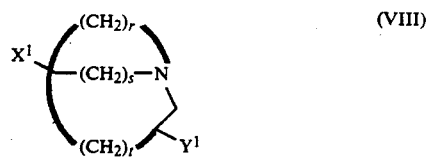

in which r,s and t are as defined in formula (I), one of $X^1$ and $Y^1$ represents hydrogen and the other represents Z″, where Z″ is a group:

in which Q' represents 3-membered divalent residue completing a 5-membered aromatic ring and comprises two or three nitrogen atoms, any amino nitrogen being unsubstituted, and salts thereof.

The compounds of the present invention enhance acetylcholine function via an action at muscarinic receptors within the central nervous system and are therefore of potential use in the treatment and/or prophylaxis of dementia.

The present invention also provides a pharmaceutical composition, which comprises a compound of formula (I) or pharmaceutically acceptable salt thereof, and a pharmaceutically acceptable carrier.

The compositions may be in the form of tablets, capsules, powders, granules, lozenges, suppositories, reconstitutable powders, or liquid preparations such as oral or sterile parenteral solutions or suspensions.

In order to obtain consistency of administration it is preferred that a composition of the invention is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

The solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol; preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The compositions may contain from 0.1% to 99% by weight, preferably from 10-60% by weight, of the active material, depending on the method of administration.

The invention also provides a method of treatment and/or prophylaxis of dementia in mammals including humans, which comprises administering to the sufferer an effective amount of a compound of formula (I) or a pharmaceutically acceptable salt thereof.

The dose of the compound used in the treatment of such disorders will vary in the usual way with the seriousness of the disorders, the weight of the sufferer, and the relative efficacy of the compound. However, as a general guide suitable unit doses may be 0.05 to 100 mg. for example 0.2 to 50 mg; and such unit doses may be administered more than once a day, for example two or three times a day, so that the total daily dosage is in the range of about 0.01 to 5 mg/kg; and such therapy may extend for a number of weeks or months.

Within the above indicated dosage ranges no toxicological effects are indicated for the compounds of the invention.

In a further aspect the invention provides a compound of formula (I) or a pharmaceutically acceptable salt thereof for use as an active therapeutic substance.

The invention further provides a compound of formula (I) or a pharmaceutically acceptable salt thereof, for use in the treatment and/or prophylaxis of dementia.

In another aspect the invention provides the use of a compound of formula (I) or a pharmaceutically acceptable salt thereof for the preparation of a medicament for the treatment and/or prophylaxis of dementia.

The following examples illustrate the invention and the 1 following descriptions illustrate the preparation of intermediates thereto.

DESCRIPTION 1

(±) Ethyl 1-(2-chloroethyl)-3-piperidylcarboxylate (D1)

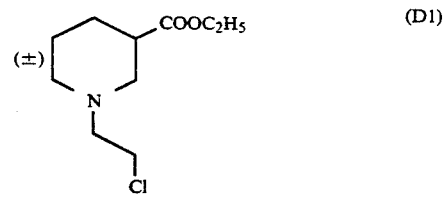

A solution of ethyl 3-piperidylcarboxylate (100 g, 0.64 mole) in acetone (800ml) was treated with 1-bromo-2-chloroethane (106.5 ml, 1.28 mole) and anhydrous potassium carbonate (138 g, 1.00 mole) and the mixture stirred at room temperature for 24 h. The mixture was concentrated in vacuo and the residue treated with water (300 ml) and extracted with ether (2×200 ml). The combined ether extracts were dried ($Na_2SO_4$) and concentrated in vacuo to leave a yellow oil, which was purified by chromatography on silica gel eluting with 50% ether/60-80 petrol to give the title compound (D1) as a pale yellow oil (78.2 g, 56%).

$^1$H Nmr ($CDCl_3$) δ: 1.25 (3H, t, J=7Hz), 1.40–3.10 (11H, m), 3.58 (2H, t, J=7Hz), 4.15 (2H, q, J=7Hz).

DESCRIPTION 2

(±) Ethyl 1-azabicyclo[3.2.1]oct-5-ylcarboxylate (D2)

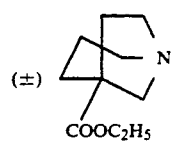

A solution of diisopropylamine (33.6 ml, 0.24 mole) in dry ether (1500 ml) at −65° C. under nitrogen was treated with 1.5 M n-butyllithium in hexane (150 ml, 0.225 mole) and the solution stirred for 15 mins, before adding N,N,N',N'-tetramethylethylenediamine (68 ml, 0.45 mole). After stirring for a further 15 mins, the solution was treated with a solution of (±) ethyl 1-(2-chloroethyl)-3-piperidylcarboxylate (D, 44.7 g, 0.204 mole) in dry ether (100 ml) and the mixture allowed to warm up to room temperature over 2 h. The reaction mixture was treated with potassium carbonate solution (300 ml) and the ether layer separated, dried (Na2SO4) and concentrated in vacuo to leave an orange oil. This was purified by chromatography on silica gel eluting with 10% methanol/chloroform to give the title compound (D2) as a yellow oil (31.9 g, 84%), b.p. 120°–130° C. at 0.4mm (Kugelröhr apparatus).

¹H Nmr (CDCl3) δ: 1.25 (3H, t, J=7Hz), 1.10–2.20 (6H, m), 2.60–3.25 (6H, m), 4.20 (2H, q, J=7Hz).

DESCRIPTION 3

(±) 1-Azabicyclo[3.2.1]oct-5-yl-N-methoxy-N-methylcarboxamide (D3)

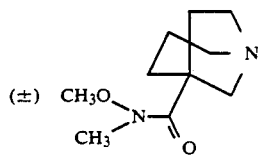

(±) Ethyl-1-azabicyclo[3.2.1]oct-5-ylcarboxylate (D2, 5 g, 0.027 mole) in hydrochloric acid (5 N, 150 ml) was heated under reflux for 1.5 h. The reaction was then concentrated in vacuo to a hygroscopic solid which was dissolved in thionyl chloride (100 ml) and heated under reflux for 0.5 h. The mixture was then concentrated in vacuo to a gum, which was freed from excess thionyl chloride by co-evaporation with toluene. The residue was dissolved in absolute chloroform (100 ml) and treated with N,O-dimethylhydroxylamine hydrochloride (2.92 g, 0.030 mole). After cooling to 0° C. pyridine (10.9 ml, 0.135 mole) was added dropwise. The reaction was allowed to warm to room temperature and stirred for 1 h. The reaction mixture was poured into saturated aqueous potassium carbonate solution (100 ml) and the mixture was extracted with chloroform (4×100 ml). The combined organic extracts were dried (Na2SO4) and evaporated to give an oil which was distilled in vacuo to afford the title compound (D3) (3.77 g, 69%) b.p. 160° C. at 0.5 mmHg.

¹N-Nmr (CDCl3) δ: 1.47 (1H, m), 1.68–2.13 (7H, m), 2.78–3.15 (6H, m), 3.17 (3H, s), 3.67 (3H, s).

DESCRIPTION 4

(±) 1-Azabicyclo[3.2.19 oct-5-yl carboxaldehyde (D4)

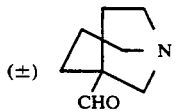

(±) 1-Azabicyclo[3.2.1]oct-5-yl-N-methoxy-N-methyl carboxamide (D3, 10 g, 0.05 mole) in dry THF (250 ml) was treated with diisobutyl aluminium hydride (43 ml of a 1.5 M solution in toluene 0.065 mole) at −60° C. The reaction mixture was allowed to warm to −20° C. over a period of 1.5 h. The reaction mixture was cooled to −60° C. and poured into 5 N hydrochloric acid at −20° C. The reaction mixture was concentrated in vacuo to remove excess tetrahydrofuran and then partitioned between saturated aqueous potassium carbonate and chloroform. The organic phase was separated and concentrated in vacuo to a gum. Kugelröhr distillation afforded the title compound b.p. 140–150 at 0.5mm (D4) (5.5 g, 0.0395 mole, 80%).

¹H NMR δ: 1.5–2.2 (6H, m), 2.7–3.2 (6H, m), 9.55 (1H, s).

DESCRIPTION 5

(±) 5-(2,2-Dibromoethenyl)-1-azabicyclo[3.2.1]octane (D5)

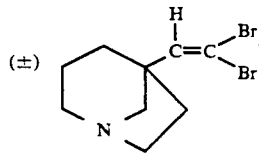

A solution of (±) 1-azabicyclo[3.2.1]oct-5-ylcarboxaldehyde aldehyde (D4, 5 g, 0.036 mol) in dichloromethane (25 ml) was added at room temperature to a reaction mixture prepared by stirring together triphenyl phosphine (18.8 g, 0.072 mol), carbon tetrabromide (23.6 g, 0.072 mol) and zinc powder (4.68 g, 0.072 mol) in dichloromethane (150 ml) for 24 h at room temperature. After the addition, the solution was stirred for a further 2 h and saturated aqueous potassium carbonate solution (50 ml) added. The solution was then filtered through celite and the organic layer separated. The aqueous layer was re-extracted with dichloromethane and the combined organic extracts dried (Na2SO4) and concentrated in vacuo to a gum. The gum was extracted with ether to afford the title compound contaminated with a little triphenyl phosphine oxide (10 g, 95%). A small portion was chromatographed on silica in a gradient of 20–40% methanol in chloroform. The title compound (D5) eluted in 30% methanol/chloroform to give the pure compound which crystallised from ether/petrol as needles.

m.p. 35°–36° C.

¹H NMR (CDCl3) δ: 1.55–2.05 (5H, m), 2.15–2.3 (1H, m), 2.85–3.3 (6H, m), 6.7 (1H, s).

DESCRIPTION 6

(±) 5-Ethynyl-1-azabicyclo[3.2.1]octane (D6)

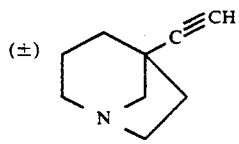

A solution of crude (±) 5-(2,2-dibromoethenyl)-1-azabicyclo[3.2.1]octane (10 g, 34 mM) (D5) in dry THF (200 ml) was cooled to −78° C. under nitrogen and treated with n-butyl lithium in hexane (49 ml of a 1.6 molar solution, 0.078 mol). The solution was stirred at this temperature for 1 h and then allowed to warm to room temperature over a period of 1 h. The reaction mixture was then cooled to −70° C. and quenched by the addition of acetic acid (10 ml). The solution was then concentrated in vacuo to a gum and the residue partitioned between chloroform and saturated aqueous potassium carbonate solution. The organic phase was separated, dried ($Na_2SO_4$) and concentrated in vacuo to a gum which was distilled in vacuo to afford the title compound (D6, 2.5 g, 51%) as a colourless oil (B.pt 110°-120° at 0.5 mM) which crystallised on standing m.p. 41°-42° C.

$^1$H NMR ($CDCl_3$) δ: 1.35-1.5 (1H, m), 1.6-2.1 (5H, m), 2.15 (1H, s, CH), 2.7-2.95 (5H, m), 3.0-3.15 (1H, m). $^{13}$C NMR ($CDCl_3$) δ: 19.4 (C-4), 36.9 (C-5), 37.1, 38.3 (C-3 and C-6), 52.5, 54.5 (C-2 and C-7), 66.1 (C-8), 68.9 (CH), 89.2 (C).

DESCRIPTION 7

N-Benzyl-N-((trimethylsilyl)methyl]amine (D7)

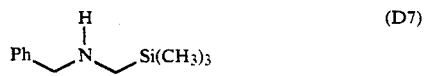

A mixture of chloromethyltrimethylsilane (325 g, 370 ml, 2.65 mole) and benzylamine (835 g, 850 ml, 7.78 mole) was heated at 120° C. (oil bath temperature) for 2 h. A white solid began appearing after only 10 minutes and a viscous mixture eventually resulted. The reaction mixture was allowed to cool, then basified with potassium carbonate solution and extracted twice with ether. The combined extracts were dried ($Na_2SO_4$) and concentrated in vacuo to leave a yellow oil, which was purified by distillation. The excess benzylamine was removed in the first fractions (b.p. 47°-62° C. at 2 mmHg). The title compound (D7) was obtained as a colourless oil (380 g, 74%) b.p. 75°-80° C. at 2 mmHg.

$^1$H NMR ($CDCl_3$) δ: 0.10 (9H, s), 1.40 (1H, br.s, NH), 2.10 (2H, s), 3.85 (2H, s), 7.27-7.43 (5H, m).

DESCRIPTION 8

N-Benzyl-N-(methoxymethyl)-N-[(trimethylsilyl)methyl]amine (D8)

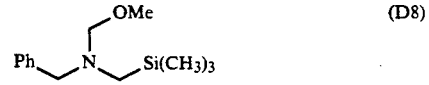

A stirred 37% aqueous formaldehyde solution (230 g, 215 ml, 2.8 mole) was cooled to −5° C. and treated dropwise over 20 minutes with N-benzyl-N-[(trimethylsilyl)methyl]amine (D7, 380 g, 1.96 mole), whilst keeping the temperature between −5° and 0° C. After completing the addition, the mixture was treated with methanol (230 ml), saturated with potassium carbonate and stirred at room temperature for 2 h. The mixture was treated with ether (500 ml) and the organic phase separated, dried ($K_2CO_3$) and concentrated in vacuo to give a colourless oil (480 g), which was about 75% title compound (D8). This material was used in the next stage without purification.

$^1$H NMR ($CDCl_3$) δ: 0.10 (9H, s), 2.23 (2H, s), 3.30 (3H, s), 3.82 (2H, s), 4.05 (2H, s), 7.25-7.40 (5H, m).

DESCRIPTION 9

α-Formyl-γ-butyrolactone sodium salt (D9)

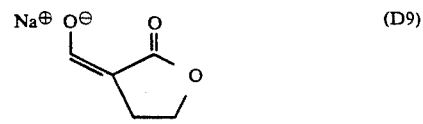

A stirred suspension of sodium hydride (300 g of 80% oil dispersion, 10 moles) in dry ether (8 L) under nitrogen was treated slowly with absolute ethanol (60 ml, 1.1 mole), followed immediately by a mixture of ethyl formate (808 ml, 10 moles) and γ-butyrolactone (770 ml, 10 moles) over about 1.25 h. The rate of addition of the reagents was regulated to give a steady reflux and evolution of hydrogen (about 220 L). After completing the addition, the mixture was stirred for a further 0.5 h and the solid then filtered off, washed with ether and dried in vacuo to give the title compound (D9) as a white solid (1.32kg, 97%).

DESCRIPTION 10

α-Methylene-γ-butyrolactone (D10)

A stirred suspension of paraformaldehyde (270 g, 9.0 mole) in THF (3.5 L) at room temperature in a 20 L flask under nitrogen was treated with α-formyl-γ-butyrolactone sodium salt (D9, 270 g, 2.0 mole). The mixture was then immediately heated to reflux temperature for 1 h. Evolution of a small quantity of gas was observed. The mixture was cooled to around 10° C., treated with saturated potassium carbonate solution (500 ml) and ether (1.5 L), and the organic layer separated, dried ($Na_2SO_4$) and concentrated in vacuo to leave a pale yellow oil. This material was distilled to give the title compound (D10) as a colourless oil (125 g, 64%) b.p. 76°-80° C. at 8 mmHg.

$^1$H NMR ($CDCl_3$) δ: 2.95-3.03 (2H, m), 4.40 (2H, t, J=7Hz), 5.69 (1H, t, J=3Hz), 6.25 (1H, t, J=3Hz).

DESCRIPTION 11

(±) 7-Benzyl-7-aza-2-oxaspiro[4,4]nonan-1-one (D11)

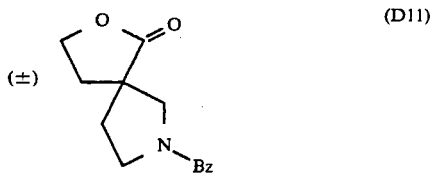

A stirred solution of N-benzyl-N-(methoxymethyl)-N-[(trimethylsilyl)methyl]amine (D8, 160 g of 75% purity, assume 0.51 mole) and α-methylene-γ-butyrolactone (D10, 50 g, 0.51 mole) in dichloromethane (1 liter) under nitrogen was cooled to 0° C. and then treated with a 1 M solution of trifluoroacetic acid in dichloromethane (50 ml, 0.05 mole), keeping the temperature below 5° C. The reaction mixture was allowed to warm to room temperature over 2 h, then washed with saturated sodium bicarbonate solution. The aqueous wash was extracted with dichloromethane and the organic solutions then combined, washed with brine, dried ($Na_2SO_4$) and concentrated in vacuo to leave a pale yellow oil. This was distilled in vacuo to give the title compound (D11) as a colourless oil (96 g, 81%) b.p. 160°–170° C. at 1 mmHg.

$^1$H NMR ($CDCl_3$) δ: 1.77–1.92 (1H, m), 2.15–2.40 (3H, m), 2.48–2.78 (3H, m), 2.85–2.98 (1H, m), 3.55–3.70 (2H, m), 4.10–4.30 (2H, m), 7.15–7.35 (5H, m).

DESCRIPTION 12

Ethyl 1-benzyl-1-azoniabicyclo[2.2.1]hect-4-ylcarboxylate bromide (D12)

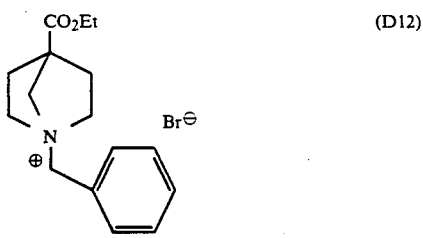

A stirred solution of 7-benzyl-7-aza-2-oxaspiro[4.4]-nonan-1-one (D11, 96 g, 0.42 mole) in ethanol (150 ml) was saturated with hydrogen bromide gas and then left to stand for 18 h. The solution was concentrated in vacuo and the residue basified with saturated potassium carbonate solution and extracted with chloroform. The organic extract was dried ($Na_2SO_4$) and concentrated in vacuo to leave a pale brown oil. This was treated with ether and the resulting solid filtered off, washed with ether and dried to give the title compound (D12) as a white solid (130 g, 91%).

DESCRIPTION 13

Ethyl 1-azabicyclo[2.2.1]hept-4-ylcarboxylate hydrobromide salt (D13)

A suspension of ethyl 1-benzyl-1-azoniabicyclo[2.2.1]hept-4-ylcarboxylate bromide (D12, 130 g, 0.38 mole) in ethanol (500 ml) was hydrogenated over 10% palladium on charcoal catalyst (8 g) at atmospheric temperature and pressure for 18 h. The catalyst was removed by filtering through celite, washing several times with hot ethanol, and the filtrate concentrated in vacuo to give the title compound (D13) as a crystalline white solid (80.1 g, 84%).

$^1$H NMR ($CD_3OD$) δ: 1.3 (3H, t, J=7Hz), 2.0–2.18 (2H, m), 2.3–2.5 (2H, m), 3.35–3.5 (2H, m), 3.45 (2H, s), 3.5–3.7 (2H, m), 4.25 (2H, q, J=7Hz).

DESCRIPTION 14

Ethyl 1-Azabicyclo[2.2.1]hept-4-ylcarboxamide (D14)

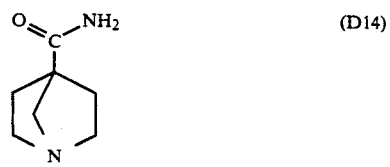

Ethyl 1-azabicyclo[2.2.1]hept-4-yl carboxylate hydrobromide salt (D13) (7.4 g, 0.03 mole) was dissolved in concentrated hydrochloric acid (55 ml) and water (20 ml) and heated under reflux for 17 h. The reaction was concentrated in vacuo and the residue azeotroped with dry toluene to afford the acid hydrochloride as a colourless solid. Thionyl chloride (100 ml) was added and the reaction heated under reflux for 4.25 h until a homogenous solution had formed. The solution was then concentrated in vacuo to a gum and azeotroped with three portions of dry toluene to remove the last traces of thionyl chloride to afford the acid chloride hydrochloride as a white solid. The acid chloride was then suspended in dry dichloromethane (100 ml) and cooled to −40° C. To this was added a solution of dichloromethane saturated with ammonia (400 ml) and the stirred solution allowed to warm to room temperature overnight. The reaction was partitioned with saturated aqueous potassium carbonate (20 ml), the organic phase separated, dried over sodium sulphate and concentrated in vacuo to afford the title compound (D14) as a colourless solid (2.63 g, 0.02 mole).

$^1$H NMR ($CD_3OD$) δ: 1.5–1.67 (2H, m, 3—CH, 5-CH), 1.9–2.08 (2H, m, 3-CH, 5-CH), 2.62–2.78 (2H, m, 2-CH, 6-CH), 2.65 (2H, s, 7-$CH_2$), 2.95–3.1 (2H, m, 2-CH, 6-CH), 5.0 ($NH_2$).

DESCRIPTION 15

1-Azabicyclo[2.2.1] hept-4-yl carbonitrile (D15)

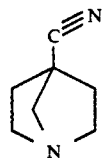

1-Azabicyclo[2.2.1]hept-4-ylcarboxamide (D14) (2.63 g, 0.02 moles) was suspended in dry tetrahydrofuran (100 ml) and pyridine (3.2 ml, 0.04 moles) added. The mixture was stirred and treated with trifluoroacetic anhydride (3.5 ml, 0.024 moles) at such a rate that the temperature did not exceed 30° C. After 15 min the reaction was quenched with water (5 ml) and concentrated in vacuo to a gum. The gum was partitioned between chloroform and saturated aqueous potassium carbonate solution. The organic phase was separated dried over sodium sulphate and concentrated in vacuo to a gum. Kugelrohr distillation afforded the title compound (D15) (2.0 g, 0.016 moles, 82%). B.pt. 125° at 1.5 mm which slowly crystallised on standing m.pt. 30°-33° C.

$^1$H NMR (CDCl$_3$) δ: 1.58-1.62 (2H, m, 3-CH, 5-CH), 1.95-2.10 (2H, m, 3-CH, 5-CH), 2.58-2.7 (2H, m, 2-CH, 6-CH), 2.75 (2H, s, 7-CH$_2$), 2.95-3.10 (2H, m, 2-CH, 6-CH).

DESCRIPTION 16

(±) 1-Benzyl-3-methoxycarbonylpyrrolidine (D16)

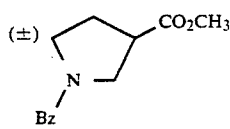

Ethyl acrylate (86 g, 1.0 mole) in dichloromethane (2 L) was cooled to 0° C. and treated with N-benzyl-N-(methoxymethyl)-N-[(trimethylsilyl)methyl]amine (D8) (300 g, 80% pure by $^1$H NMR, 1 mole) with stirring over a period of 10 min whilst maintaining the temperature between −5° C. and 0° C. A solution of trifluoroacetic acid in dichloromethane (100 ml, 1 molar) was added at such a rate that the temperature did not rise above 5° C. and the reaction allowed to warm to room temperature overnight. The solution was then washed with saturated aqueous potassium carbonate solution, dried over sodium sulphate and concentrated in vacuo to a gum. The gum was distilled in vacuo to afford the title compound (D16) as a single main fraction. Bpt 150°-160° at 8 mm (232 g, 100%).

$^1$H NMR (CDCl$_3$) δ: 2.05-2.15 (2H, m), 2.45-2.75 (3H, m), 2.75-2.85 (1H, t, J=11Hz), 3.0-3.10 (1H, q, J=11Hz), 3.60 (2H, s, CH$_2$Ar), 3.7 (3H, s, CH$_3$), 7.2-7.35 (5H, m, Ph).

DESCRIPTION 17

(±) 1-Ethoxycarbonylmethyl-3-methoxycarbonyl pyrrolidine (D17)

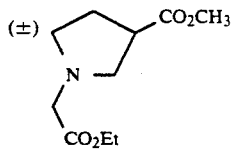

1-Benzyl-3-methoxycarbonyl pyrrolidine (D16) (232 g, 1.05 mole) was dissolved in ethanol (1 L) and treated with ethyl bromoacetate (1.84 g, 1.1 mole) and potassium carbonate (27 g, 0.2 mole) under reflux for 6 h. The reaction was then allowed to cool and was filtered. The filtrate was concentrated in vacuo to an oil which was swirled with ether to remove unreacted ethyl bromoacetate. The oil was separated from the ether and redissolved in ethanol (500 ml) and treated with acetic acid (30 ml). To this was added 10% palladium on charcoal (20 g) and the mixture stirred under an atmosphere of hydrogen until the uptake was complete. The reaction was then filtered through celite and concentrated to a gum. The gum was partitioned between dichloromethane and saturated aqueous potassium carbonate solution. The organic phase was separated dried over sodium sulphate and concentrated to a gum. Vacuum distillation afforded the title compound (D17) (132.5 g, 0.62 mole) as the main fraction. B.p. 110°-120° C. at 0.5 mm Hg.

$^1$H NMR (CDCl$_3$) δ: 1.3 (3H, t, J=8Hz, CH$_3$), 2.1-2.2 (2H, m), 2.5 (1H, q, J=8Hz), 2.75 (1H, Br S), 2.85-3.0 (1H, m), 2.05-3.2 (2H, m), 3.3 and 3.4 each (1H, d, J=16Hz), 3.7 (1H, s), 4.2 (2H, q, J=8Hz).

DESCRIPTION 18

(±) 1-Azabicyclo[2.2.1]heptan-3-one (D18)

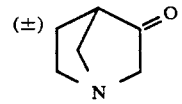

Potassium t-butoxide (165 g, 1.35 mole in dry toluene (2 L) was heated to reflux under an atmosphere of nitrogen. 1-Ethoxycarbonylmethyl-3-methoxycarbonyl pyrrolidine (D17) (132 g, 0.62 mole) was added dropwise over a period of 1 h and the reaction was refluxed for a further 2 h. The reaction was then cooled to −10° C. and acetic acid (80 ml) added with continuous stirring. The toluene solution was then repeatedly extracted with 5 N hydrochloric acid (4×500 ml) and the combined aqueous extracts heated under reflux for 10 h. The solution was concentrated to 1 L and neutralised by addition of saturated aqueous potassium carbonate solution. Extraction with dichloromethane (5×800 ml) afforded a yellow oil which was distilled in vacuo to afford the title compound (D18, 24.9 g, 0.226 mole, 36%). B.p. 80°-82° C. at 0.4 mm Hg which solidified on cooling to give a very hygroscopic solid. M.pt 40°-50° C.

$^1$H NMR (CDCl$_3$) δ: 1.73-1.85 (1H, m), 2.0-2.2 (1H, m), 2.65-2.85 (4H, m), 3.3-3.15 (3H, m)

DESCRIPTIONS 19 AND 20

(±) exo-3-Cyano-1-azabicyclo[2.2.1]heptane (D19) and
(±) endo-3-cyano-1-azabicyclo[2.2.1]heptane (D20)

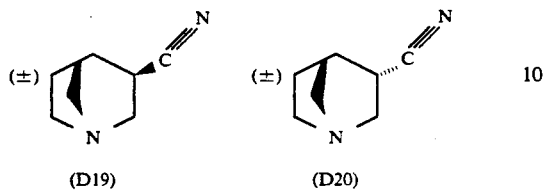

3-Oxo-1-azabicyclo[2.2.1]heptane (D18, 5.0 g, 0.045 mol) was dissolved in sodium-dried dimethoxyethane (200 ml) and tosylmethyl isocyanide (9.67 g, 1.1eq) added under nitrogen at 0° C. Dry EtOH (2.64 ml, 1.1eq) was added and the solution cooled under nitrogen to −40° C. Potassium t-butoxide (12.28 g, 2.43eq) was added portionwise under nitrogen maintaining the temperature below −20° C. The solution was then stirred at −8° C. for 2 h, allowed to warm to room temperature and stirred for 1 h. The suspension was quenched with sufficient glacial acetic acid to dissolve the precipitate and the solution then evaporated under reduced pressure to remove DME. The solution was then basified with saturated aqueous potassium carbonate and extracted with chloroform (3×500 ml). The organic extracts were dried ($Na_2SO_4$), filtered and evaporated to dryness under reduced pressure to yield a deep red oil which was purified by Kugelröhr distillation (b.p. 160° C., 10 mmHg) to yield the title compound as a clear colourless oil (2.79 g, 56%). The proportion of exo and endo isomers estimated from $^{13}C$ nmr was 1:1.25, and these were separated by column chromatography using neutral alumina and eluting with ether to ethyl acetate, to yield the title compounds as separate isomers the faster running (D19) and slower running (D20). The stereochemistry of each was confirmed by nmr analysis.

$^1H$ nmr (CDCl$_3$, 270 MHz) 1.14 (1H, m), 1.67 (1H, m), 2.22 (1H, m), 2.47 (2H, bm), 2.69 (1H, dm), 2.94 (4H, complex m).

$^{13}C$ nmr (CDCl$_3$, 67 MHz) 29.58 ($CH_2$), 32.29 (CH), 42.92 (CH), 53.80 ($CH_2$), 59.59 ($CH_2$), 60.37 ($CH_2$), 122.23 (C N).

(D20)

$^1H$ nmr (CDCl$_3$, 270 MHz) 1.63 (1H, m), 1.80 (1H, m), 2.56 (4H, complex m), 2.78 (1H, m), 2.91 (2H, complex m), 3.18 ( $^1H$, tm).

$^{13}C$ nmr (CDCl$_3$, 67 MHz) 25.68 ($CH_2$), 31.08 (CH), 40.72 (CH), 54.05 ($CH_2$), 59.16 ($CH_2$), 60.48 ($CH_2$), 121.61 (C N).

DESCRIPTION 21

1-Azabicyclo[2.2.1]hept-4-yl-N-methoxy-N-methyl carboxamide (D21)

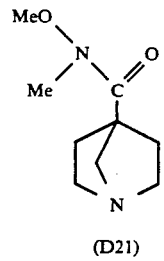

Ethyl 1-azabicyclo[2.2.1]hept-4-yl carboxylate hydrobromide salt (D13) (34 g, 0.136 mole) in concentrated hydrochloric acid (200 ml) and water (50 ml) was heated under reflux for 17 h. The solution was concentrated in vacuo to afford a white solid. Thionyl chloride (250 ml) was added and the solution heated under reflux for 3 h when a homogenous solution was obtained. The excess thionyl chloride was then removed in vacuo and the residue azeotroped with dry toluene to remove the last traces of thionyl chloride. The residue was dissolved in dry acetonitrile (250 ml) and treated with N,O-dimethyl hydroxylamine hydrochloride (16 g, 0.165 mole) and cooled to −30° C. Pyridine (53 g, 0.67 mole) was then added to the stirred reaction mixture at such a rate that the temperature did not rise above −20° C. The reaction was then allowed to warm to room temperature over 16 h. The reaction was then concentrated in vacuo to a gum and the residue partitioned between chloroform and saturated aqueous potassium carbonate solution. The organic phase was separated, dried over sodium sulphate and concentrated in vacuo to a gum. The gum was dissolved in dichloromethane and treated with decolourising charcoal filtered and reconcentrated to a gum. Recrystallisation from ether afforded 1-azabicyclo[2.2.1]hept-4-yl-N-methoxy-N-methyl carboxamide (D21) (21.2 g, 0.115 mole, 84%) as needles.

m.p. 108°–110° C.

$^1H$ NMR, 270 MHz (CDCl$_3$) δ: 1.6–1.75 (2H, m, 3,5-H), 1.85–1.95 (2H, m, 3,5-H), 2.57–2.7 (2H, m, 2,6-H), 2.75 (2H, s, 7-CH$_2$), 2.95–3.1 (2H, m, 2,6-H), 3.25 (3H, s, NMe), 3.7 (3H, s, OMe).

$^{13}C$ NMR (CDCl$_3$) δ: 33.1 (C-4), 34.0 (C-3, C-5), 55.5 (C-2, C-6), 55.6 (C-7), 61.4 (N-Me), 63.1 (OMe), 175 (C=O).

DESCRIPTION 22

4-Acetyl-1-azabicyclo[2.2.1]heptane (D22)

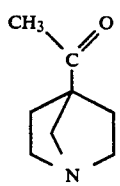

1-Azabicyclo[2.2.1]hept-4-yl-N-methoxy-N-methyl carboxamide (D21) (10 g, 0.054 mole) was dissolved in dry THF (250 ml) under nitrogen cooled to −40° C.

and treated with methyl lithium in ether (55 ml, 1 molar, 0.055 moles). The solution was allowed to warm to room temperature over a period of 1 h. Acetic acid (3.3 ml, 1eq) was added and the solution concentrated in vacuo to a gum. The residue was partitioned between chloroform and saturated aqueous potassium carbonate solution. The organic phase was separated, dried over sodium sulphate and concentrated in vacuo to a gum which was distilled in vacuo to afford 4-acetyl-1-azabicyclo[2.2.1]heptane (D22) (5.15 g, 0.037 mole, 68%).

B.P. 100–110 at 0.5 mmHg.

$^1$H NMR (CDCl$_3$) δ: 1.4–1.52 (2H, m, 3,5-H), 1.92–2.05 (2H, m, 3,5-H), 2.4 (3H, s, CH$_3$), 2.58–2.72 (4H, m), 2.98–3.1 (2H, m, 2,6-H).

$^{13}$C NMR (CDCl$_3$), 270 MHz, δ: 28.3 (CH$_3$), 34.5 (C-3, C-5), 55.5 (C-2, C-6), 62.5 (C-4), 63.4 (C-7), 210.05 (C=O).

DESCRIPTION 23

4-Chloroacetyl-1-azabicyclo[2.2.1]heptane hydrochloride (D23)

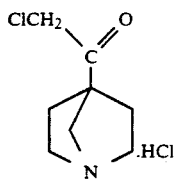

(D23)

4-Acetyl-1-azabicyclo[2.2.1]heptane (D22) (5.15 g, 0.037 mole) in ether (100 ml) was treated with hydrogen chloride gas until the precipitation of the hydrochloride salt was complete. The ether was then removed in vacuo and the residue dissolved in methanol (100 ml) and treated at 0° C. with a solution of chlorine in methanol (2.9 g, 0.041 mole, in 50 ml), and the solution allowed to warm to 20° C. over 4 h. The solution was then concentrated in vacuo to a gum which was crystallised from methanol/ether to give the title compound (D23) (5.5 g, 0.026 mole, 71%) as needles.

m.p. 210°–220° C. dec.

$^1$H NMR ((CD$_3$)$_2$SO) 250 MHz δ: 1.85–2.0 (2H, m, 3,5-H), 2.13–2.3 (2H, m, 3,5-H), 3.2–3.45 (6H, m), 4.88 (2H, s, CH$_2$Cl).

$^{13}$C NMR ((CD$_3$)$_2$SO) δ: 29.9, 48.1, 51.7 56.5. 58.5, 199.

DESCRIPTION 24

4-(Triphenylphosphinemethylenecarbonyl)-1-azabicyclo [2.2.1]heptane (D24)

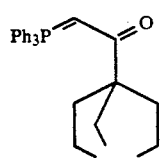

(D24)

A solution of 4-chloroacetyl-1-azabicyclo[2.2.1]heptane hydrochloride (D23) (4 g, 0.0191 mole) in dry acetonitrile (100 ml) was treated with triphenyl phosphine (10 g, 0.037 mole) under nitrogen at reflux for 48 h. The solution was then concentrated in vacuo to a gum which was partitioned between chloroform and saturated aqueous potassium carbonate solution. The organic phase was separated and dried over sodium sulphate and concentrated in vacuo to a gum. This was swirled with ethyl acetate when the title compound (D24) crystallised as needles m.pt 203°–205° C. The mother liquors were concentrated and chromatographed on alumina in a gradient of 2–20% methanol in ethyl acetate when a further portion of the title compound (D24) eluted as the slowest running fraction in 15% methanol in ethyl acetate to give a total yield of (6.4 g, 16 mmole, 83%).

$^1$H NMR (CDCl$_3$) δ: 1.4–1.55 (2H, m, 3,5-H), 1.9–2.1 (2H, m, 3,5-H), 2.53–2.7 (4H, m), 2.9–3.1 (2H, m), 3.7 (1H, d, J=26Hz), 7.3–7.7 (15H, m, Ar).

$^{13}$C NMR (CDCl$_3$) δ: 35.3 (c-3,5), 50.5 (d, J=108Hz, CH=P), 55.5 (C-2,6), 58.7 (d, J=13Hz, C-4), 63.4 (C-7), 127.2 (d, J=91), 128.8 (d, J=12Hz), 132.0 (d, J=3Hz), 133.0 (d, J=10Hz), 192.8 (C=O).

DESCRIPTION 25

4-(1-m-Nitrobenzoyl-1,2,3-triazol-4-yl)-1-azabicyclo-[2.2.1]heptane (D25)

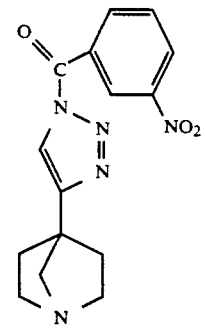

(D25)

A solution of 4-(triphenylphosphinemethylenecarbonyl)-1-azabicyclo [2.2.1]heptane (D24) (4 g, 0.01 mole) in dry acetonitrile (80 ml) was treated with m-nitrobenzoylazide* (3.8 g, 0.020 mole) under nitrogen and the solution heated to reflux for 2 h. The solution was then concentrated in vacuo to a gum which was dissolved in ethyl acetate (30 ml) and allowed to stand at 0° C. overnight when the title compound (D25) (1.35 g, 0.0043 mole, 43%) crystallised out.

*Org. Syn. Vol. IV p715.

M.pt. 160°–162° C.

$^1$H NMR (DMSO) δ: 1.82–2.0 (2H, m, 3,5-H), 2.1–2.25 (2H, m, 3,5-H), 3.06–3.22 (4H, m), 3.3–3.45 (2H, m, 2,6-H), 7.5 (1H, m, Ar), 7.9 (1H, s, 5'H), 8.25–8.35 (2H, m, Ar), 8.6–8.65 (1H, m, Ar).

$^{13}$C NMR (DMSO) δ: 33.8 (C-3,5), 44.7 (C-4), 52.6 (C-2,6), 61.6 (C-7), 123.4, 124.8, 128.0. 129.5. 135.2 (C-5), 139.0, 143.85, 147.6 (Ar-C), 167.2 (C=O).

DESCRIPTION 26

4-(2H-1,2,3-Triazol-4-yl)-1-azabicyclo[2.2.1]heptane (D26)

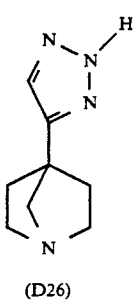

(D26)

A solution of 4-(1-m-nitrobenzoyl-1,2,3-triazol-4-yl)-1-azabicyclo[2.2.1]heptane (D25) (1 g, 0.0032 mole) in methanol (50 ml) was saturated with ammonia gas. The solution allowed to stand at room temperature for 3 days and then concentrated in vacuo to a gum. The gum was chromatographed on alumina in a gradient of 10-20% methanol in chloroform, elution with 15% methanol in chloroform produced a gum which crystallised from ethyl acetate to afford the title compound (D26, 450mg, 0.0027 mole, 85%).

M.p. 164°-166° C.

$^1$H NMR (DMSO) δ: 1.45-1.6 (2H, m, 3,5-H), 1.8-1.95 (2H, m, 3,5-H), 2.49-2.65 (4H, m), 2.83-2.97 (2H, m, 2,6-H), 7.7 (1H, s, ArH).

DESCRIPTION 27

(±) 1-Azabicyclo[2.2.2]oct-3-yl-N-methoxy-N-methyl carboxamide (D27)

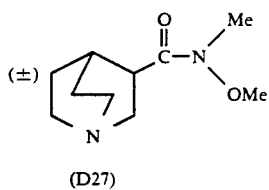

(D27)

Methyl quinuclidine-3-carboxylate (49 g, 0.268 mole) in 5 N hydrochloric acid (1 L) was heated under reflux for 8 h and then concentrated in vacuo to a gum. This was then treated with excess thionyl chloride (250 ml) and heated under reflux for 0.5 h when a homogenous solution was obtained and the evolution of sulphur dioxide ceased. The solution was then concentrated in vacuo to a gum which was azeotroped repeatedly with toluene to remove the last traces of thionyl chloride. The crystalline acid chloride hydrochloride was suspended in dry acetonitrile (250 ml) and cooled to −10° C. To this was added dry N-methyl-O-methyl hydroxylamine hydrochloride (28.5 g, 0.295 mole) and pyridine (106 g, 1.34 mole) added dropwise at such a rate that the temperature did not rise above −5° C. The solution was then allowed to warm to 25° C. over a period of 1 h. Chloroform (500 ml) was added and the solution shaken with saturated aqueous potassium carbonate. The organic phase was separated, dried over sodium sulphate and concentrated in vacuo to a gum. Vacuum distillation afforded the title compound (D27) (17.7 g, 0.089 moles, 33%).

b.p. 100°-110° C. at 0.5 mm which solidified on standing.

$^1$H NMR CDCl$_3$ δ: 1.3-1.45 (1H, m), 1.5-1.7 (2H, m), 1.75-1.9 (1H, m), 2.0-2.1 (1H, m), 2.62-3.08 (6H, m), 3.2 (3H, s), 3.23-3.33 (1H, m), 3.7 (3H, s).

DESCRIPTION 28

(±) 3-Acetyl-1-azabicyclo2.2.2]octane (D28)

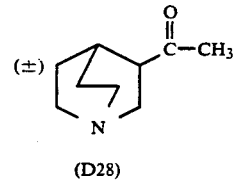

(D28)

(±) 1-Azabicyclo[2.2.2]oct-3-yl-N-methoxy-N-methyl carboxamide (D27) (16.3 g, 0.082 mole) in dry tetrahydrofuran (250 ml) at −50° C. under an atmosphere of nitrogen was treated with methyl lithium in ether (60.4 ml of a 1.5 molar solution) over a period of 25 mins. The reaction was then allowed to warm to −20° C. and held at this temperature for 15 minutes, and then re-cooled to −50° C. The reaction was then quenched by the addition of glacial acetic acid (5.4 ml) and poured on to saturated potassium carbonate (150 ml) and chloroform (500 ml). The organic layer was separated and the aqueous solution re-extracted with chloroform (2×250 ml). The combined organic extracts were concentrated in vacuo to a gum which was distilled. Bp −94° C. at 1 mmHg to afford the title compound (D28) (11.66 g, 0.076 mole, 92%).

$^1$H NMR (DMSO) δ: 1.43-1.57 (1H, m), 1.57-1.73 (1H, m), 1.8-2.0 (2H, m), 2.3 (3H, s), 2.45-2.55 (1H, m), 2.9-3.2 (6H, m), 3.37-3.5 (1H, m).

$^{13}$C NMR (DMSO) δ: 20.2, 22.7, 24.5, 28.5, 45.8 (2C), 46.6, 47.16, 208.3

DESCRIPTION 29

(±) 3-(Triphenylphosphinemethylenecarbonyl)-1-azabicyclo2.2.2]octane (D29)

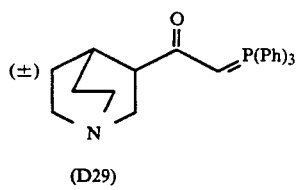

(D29)

A solution of (±) 3-acetyl-1-azabicyclo[2.2.2]octane (D28) (5.44 g, 0.035 mole) in ether (100 ml) was treated with hydrogen chloride gas until the precipitation of the hydrochloride salt was complete. The solution was then concentrated in vacuo to a gum and re-dissolved in methanol (50 ml). The solution was cooled to 0° C. and treated with a solution of chlorine (2.94 g, 0.042 mole) in methanol (100 ml) at 0° C. and the solution allowed to warm to room temperature over 4 h. The solution was then concentrated in vacuo to a gum which was dissolved in dry acetonitrile (100 ml) and treated with triphenyl phosphine (20 g, 0.077 mole) and heated under reflux for 24 h. The reaction mixture was concentrated in vacuo to a gum which was partitioned between chloroform and saturated aqueous potassium carbonate solution. The organic phase was separated, dried over sodium sulphate and concentrated in vacuo to a gum. Chromatography on basic alumina in a gradient of 4–20% methanol in ethyl acetate gave a fraction eluting in 15–20% methanol in ethyl acetate which crystallised from ethyl acetate/ether to give the title compound (D29, 2.15 g, 0.0056 moles, 16%). m.p. 210°–215° C.

$^1$H NMR (DMSO) δ: 1.15–1.3 (1H, m), 1.43–1.6 (2H, m), 1.6–1.75 (1H, m), 2.04–2.13 (1H, m), 2.42–2.75 (6H, m), 3.08–3.20 (1H, dd, J=5Hz, J TM 15Hz), 3.65 (1H, d, J=26Hz), 7.48–7.74 (15H, m).

DESCRIPTION 30

(±) 3-(2H-1,2,3-Triazol-4-yl)-1-azabicyclo2.2.2]octane (D30)

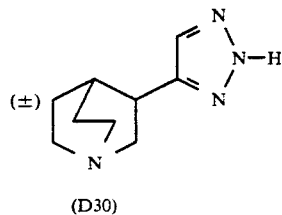

(D30)

A solution of 3-(triphenylphosphinemethylenecarbonyl)-1-azabicyclo[2.2.2]octane (D29) (8 g, 0.00193 mole) in acetonitrile (150 ml) at reflux was treated with m-nitro benzoylazide* (7.44 g, 0.0386 mole) under nitrogen at reflux temperature for 2 h. The solution was then concentrated in vacuo to a gum which was chromatographed on alumina in a gradient 5–20% methanol in chloroform. Elution with 15% methanol in chloroform yielded a gum which crystallised from ethyl acetate to afford the title compound (D30, 1.95 g, 0.0109 mole, 52%) as needles.
*Org. Syn. Vol. IV P.715.

m.pt 172°–174.5° C.

$^1$H NMR (DMSO) 270MHz δ: 1.28–1.44 (1H, m), 1.44–1.6 (1H, m), 1.65–1.8 (2H, m), 1.93–2.0 (1H, m), 2.7–2.94 (4H, m), 3.0–3.15 (2H, m), 3.17–3.33 (1H, m), 3.8 (1H, Brs), 7.84 (1H, s).

$^{13}$C NMR (DMSO) (67.8MHz) δ: 21.0, 27.0 (C-5,8), 26.6, 32.4 (C-3,4), 46.6, 47.0, 52.7 (C-2,6,7), 128.6 (C-5'), 147.9 (C-4').

DESCRIPTION 31

(±) 5-Acetyl-1-azabicyclo[3.2.1]octane (D31)

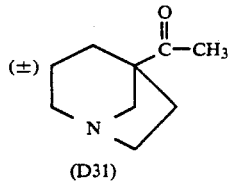

(D31)

A solution of (±) 1-azabicyclo[3.2.1]oct-5-yl-N-methyl-N-methoxycarboxamide (D3) (22.0 g; 0.11 mole) in dry ether (500 ml) was cooled to −30° C. under nitrogen and treated dropwise with methyl lithium (80.0 ml of a 1.4 M solution in diethyl ether; 0.11 mole). The rate of addition was controlled to ensure that the temperature of the reaction remained below 0° C. After stirring for 1 h at −10° C. the reaction was quenched by the addition of excess glacial acetic acid, while maintaining the temperature below −10° C. The ether solution was washed with a saturated solution of potassium carbonate. After extraction of the aqueous phase with chloroform (3×200 ml) the combined organic layers were dried over sodium sulphate and concentrated in vacuo.

Distillation afforded the title compound (D31) (15.0 g; 88%), bp 150° C. at 0.4 mmHg.

$^1$H Nmr (CDCl$_3$) δ: 1.45–1.55 (1H, m), 1.65–1.90 (4H, m), 2.00–2.10 (1H, m), 2.15 (3H, s), 2.65–3.00 (5H, m), 3.05–3.20 (1H, m).

Ir (film) νC=O 1695cm$^{-1}$.

DESCRIPTION 32

(±) 5-(Triphenylphosphinemethylenecarbonyl)-1-azabicyclo[3.2.1]octane (D32)

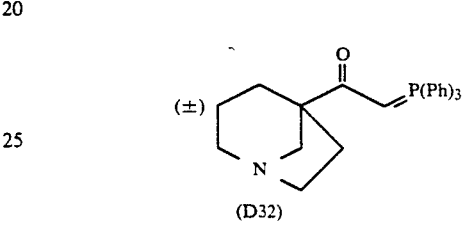

(D32)

A solution of (±) 5-acetyl-1-azabicyclo[3.2.1]octane (D31) (5 g, 0.03 mole) in ether (50 ml) was treated with hydrogen chloride gas until the precipitation of the hydrochloride salt was complete. The solution was then concentrated in vacuo to a gum and dissolved in methanol (50 ml). A solution of chlorine (2.13 g, 0.03 mole) in methanol (100 ml) was added at 0° C. and the solution allowed to warm to 20° C. over 1 h when the solution had decolourised. The methanol was then removed in vacuo to afford a colourless gum (6.6 g) which was dissolved in dry acetonitrile (100 ml) and treated with triphenylphosphine (15.7 g, 0.06 mole) under nitrogen at reflux for 16 h. The solution was then concentrated in vacuo to a gum which was partitioned between chloroform and saturated aqueous potassium carbonate solution. The organic phase was separated, dried over sodium sulphate and concentrated in vacuo to a gum which was chromatographed on alumina in a gradient of 5–20% methanol in ethyl acetate. Elution with 15% methanol in ethyl acetate afforded a gum which crystallised from ether to yield (D32) (3.7 g, 0.009 mole, 30%). m.p. 206°–208° C.

$^1$H NMR (CDCl$_3$) δ: 1.4–1.52 (1H, m), 1.7–2.0 (4H, m), 2.08–2.22 (1H, t, d, J=11Hz, J=5Hz), 2.74–2.94 (4H, m), 2.97–3.14 (2H, m), 3.7 (1H, d, J=26.5Hz), 7.4–7.7 (15H, m, Ar).

$^{13}$C NMR (CDCl$_3$) δ: 20.8 (C-3), 35.5 and 35.8 (C-4,6), 49.6 (d, J=109Hz, CH=P), 52.9, 55.32, 64.5 (C-2,7,8), 53.3 (d, J=13Hz, C-5), 127.9 (d, J=90Hz), 129.2 (d, J=12Hz), 132.3 (d, J=3Hz), 133.4 (d, J=10Hz), 196.8 (d, J=2Hz, C=O).

DESCRIPTION 33

(±) 5-(2H-1,2,3-Triazol-4-yl)-1-azabicyclo[3.2.1]octane (D33)

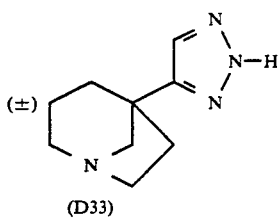

(D33)

A solution of (±) 5-(triphenylphosphinemethylenecarbonyl)-1-azabicyclo[3.2.1]octane (D32) (3 g, 0.0072 mole), in dry acetonitrile (80 ml) was treated with m-nitrobenzoylazide* (2.79 g, 0.0144 mole) under nitrogen at reflux for 2 h. The reaction was then concentrated in vacuo to a gum which was chromatographed on basic alumina in a gradient of 5–20% methanol in chloroform to give a gum which crystallised from methanol/ether as needles to afford the title compound (D33) (0.68 g, 0.0038 mole, 54%).
*Org. Syn. vol. IV, p.715.

m.p. 70°–75° C.

$^1$H NMR (CD30D) 270 MHz δ: 1.7–1.9 (1H, m), 2.0–2.25 (3H, m), 2.28–2.41 (2H, m), 3.02–3.42 (6H, m), 7.8 (1H, s).

$^{13}$C NMR (CD$_3$OD) 67 MHz δ: 20.2 (C-4), 37.2 (C-3,6), 42.4 (C-5), 52.5, 54.8, 65.03 (C-2,7,8), 127.4 (C5'), 150.7 (C-4').

DESCRIPTION 34

(±) cis-2-Benzyl-(3H)-hexahydropyrano[3,4-c]pyrrol-4-one (D34)

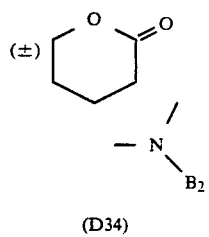

(D34)

To a stirred solution of 5,6-dihydro-2H-pyran-2-one* (136 g, 1.39 mole) in dichloromethane (2 L) at −20° C. was added N-benzyl-N-(methoxymethyl)-N-((trimethylsilyl)methyl)amine (80%, pure) (D8, 450 g, 1.5 mole). To this solution was added trifluoroacetic acid in dichloromethane (140 ml, 1 molar solution) at −20° C. The reaction was then transferred at −20° C. under a small positive pressure of nitrogen via a double ended needle to a second flask on a water bath at 30° C. As the cold mixture warmed up an exothermic reaction occurred and the rate of addition was controlled to maintain gentle reflux. When the addition was complete and the reaction had subsided the solution was allowed to stand at room temperature for 2 h. The reaction was then washed with saturated aqueous potassium carbonate solution, dried over sodium sulphate and concentrated in vacuo to a gum. Vacuum distillation afforded a single main fraction b.p. 180–1900 5 mmHg (D34) (180.9 g, 0.73 mole, 56%).

*Org. Syn, Vol. 56, p.49.

$^1$H NMR (CDCl$_3$) δ: 1.55–1.75 (1H, m), 1.95–2.10 (1H, m), 2.23–2.34 (1H, m), 2.63–3.0 (4H, m), 3.05–3.2 (1H, m), 3.55 and 3.65 each (1H, d, J=12Hz), 4.22 (1H, t, J=2Hz), 4.35–4.48 (1H, m), 7.30 (5H, br.s).

$^{13}$C NMR CDCl$_3$ δ: 8.4, 35.1, 42.1, 57.5, 59.6, 60.2, 67.2, 127.2, 28.4, 128.7, 138.6, 173.3.

DESCRIPTION 35

(±) endo Ethyl-1-azabicyclo[2.2.1]hept-3-ylcarboxylate (D35)

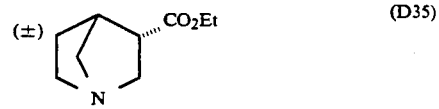

(±) cis-2-Benzyl-(3H)-hexahydropyrano[3,4-c]pyrrol-4-one (D34) (180 g, 0.78 mole) in ethanol (400 ml) was stirred and cooled to 0° C. and hydrogen bromide gas introduced at such a rate that the temperature did not rise above 20° C. until the solution was saturated. The reaction was allowed to stand at room temperature for h. The reaction was then poured into a well stirred mixture of chloroform (2 L) and saturated aqueous potassium carbonate solution (1.5 L) which was cooled by the addition of solid carbon dioxide. The organic layer was separated and the aqueous layer re-extracted with chloroform (4×1 L). The combined organic extracts were dried over sodium sulphate concentrated in vacuo to a gum. The gum was then stirred with ether (3×750 ml) to remove any unreacted starting material and the ether insoluble gum dissolved in ethanol (1 L). Palladium on charcoal 10% (20 g) was then added and the mixture stirred under an atmosphere of hydrogen at 50° C. for 6 h when the uptake of hydrogen was complete. The reaction was then filtered through kieselguhr and concentrated in vacuo to a gum. This was partitioned between chloroform and saturated aqueous potassium carbonate solution. The organic phase was separated, dried over sodium sulphate and concentrated in vacuo to afford the title compound (D35) (75 g, 0.44 mole, 56%) as an oil b.p. 90°–95° C.0.5 mmHg.

$^1$H NMR (CDCl$_3$) δ: 1.28 (3H, t, J=8Hz), 1.3–1.45 (1H, m), 1.5–1.65 (1H, m), 2.5–2.7 (3H, m), 2.85–3.05 (5H, m), 4.15 (2H, q, J=8Hz).

$^{13}$C NMR CDCl$_3$ δ: 14.2 (CH3), 25.3 (C-5), 40.9 and 46.3 (C-3 and C-4), 53.2, 55.7, 60.5, 61.2, (C-2, C-6, C-7, CH$_2$O), 173.2 (C=O).

DESCRIPTION 36

(±) endo-1-Azabicyclo(2.2.1]hept-3-yl-N-methyl-N-methoxycarboxamide (D36)

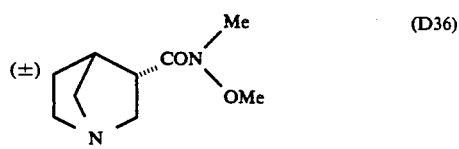

(±) endo Ethyl-1-azabicyclo[2.2.1]hept-3-ylcarboxylate (D35) (10 g, 0.059 mole) was dissolved in 5 N hydrochloric acid (100 ml) and heated under reflux for 4 h and the reaction mixture then concentrated in vacuo to a gum. This was then dissolved in thionyl chloride (50 ml) and heated under reflux for 15 min when the evolution of gases had ceased. The reaction was then concentrated in vacuo to a gum which was azeotroped with dry toluene to remove the last traces of thionyl chloride. The residue in dry acetonitrile (100 ml) was treated with N,O-dimethyl hydroxylamine hydrochloride (5.72 g, 0.065 mole) at −20° C. and pyridine (23 g, 0.3 mole) slowly added with stirring. The solution was allowed to warm to 20° C. and stirred at this temperature for 3 h. The solution was then concentrated in vacuo to a gum which was partitioned between chloroform and saturated aqueous potassium carbonate solution. The organic phase was separated, dried over sodium sulphate and concentrated in vacuo to a gum. Kugelröhr distillation afforded the title compound (D36) (3.6 g, 0.02 mole, 35%).

b.p. 150° C. at 0.5 mm.

$^1$H NMR (CDCl$_3$) 250 MHz δ: 1.35–1.45 (2H, m), 2.4–2.5 (1H, m), 2.55–3.15 (7H, m), 3.2 (3H, s), 3.73 (3H, s).

$^{13}$C NMR (CDCl$_3$) 67 MHz δ: 25.2 (C-5), 32.3 (C-4), 40.9 (NCH$_3$), 44.1 (OCH$_3$), 53.7, 56.3 and 62.3 (C-2,6,7), 61.2 (C-3), 128.3 (C=O).

DESCRIPTION 37

(±) endo-3-Acetyl-1-azabicyclo[2.2.1] heptane (D37)

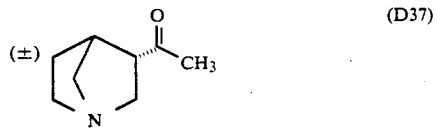

(±) endo-1-Azabicyclo[2.2.1]hept-3-yl-N-methyl-N-methoxycarboxamide (D36) (3.6 g, 0.0195 mole) in dry THF (100 ml) under nitrogen was cooled to −50° C. and treated dropwise with methyl lithium in ether (20 ml of a 1 molar solution) (0.02 mole) and the reaction allowed to warm to −20° C. over a period of 0.5 h. The solution was then cooled to −50° C. and acetic acid (1 ml) added to quench the reaction. The solution was then concentrated in vacuo to a gum which was partitioned between saturated aqueous potassium carbonate solution and chloroform. The organic phase was separated, dried over sodium sulphate and concentrated in vacuo to a gum which was distilled in a kugelrohr to afford the title compound (D37) (2.8 g, 0.02 mole, 100%). Bpt 140° C. at 1.0 mmHg.

$^1$H NMR (CDCl$_3$) 250 MHz δ: 1.08–1.22 (1H, m, 5-H), 1.38–1.54 (1H, m, 5-H), 2.19 (3H, s, CH$_3$), 2.44–3.05 (8H, m).

$^{13}$C NMR (CDCl$_3$) 67 MHz δ: 25.1 (C-5), 30.65 (CH$_3$), 41.0 (C-4), 53.8, 54.4 and 62.2 (C-2,6,7), 55.0 (C-3), 208.4 (C=O).

DESCRIPTION 38 AND 39

(±) endo-3-(Triphenylphosphinemethylenecarbonyl)-1-azabicyclo[2.2.1]heptane (D38) and (±) exo-3-(Triphenylphosohinemethylenecarbonyl)-1-azabicyclo[2.2.1]heptane (D39)

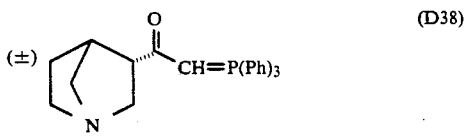

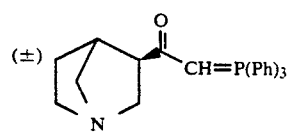

(±) endo-3-Acetyl-1-azabicyclo[2.2.1]heptane (D37) (2.8 g, 0.002 mole) in ether (50 ml) was treated with excess hydrogen chloride at room temperature and then concentrated in vacuo to a gum. The gum was dissolved in methanol (50 ml) and treated with chlorine in methanol (1.5 g in 50 ml, 0.021 mole) at 0° C. The solution was allowed to warm to room temperature over a period of 4 h when the colour of the chlorine had discharged. The solution was then concentrated in vacuo to a gum which was treated with triphenyl phosphine (10 g, 0.038 mole) in dry acetonitrile in an atmosphere of nitrogen under reflux for 16 h. The solution was then concentrated in vacuo to a gum which was partitioned between chloroform and saturated aqueous potassium carbonate solution. The organic phase was separated, dried over sodium sulphate and concentrated in vacuo to a gum which was chromatographed on basic alumina in a gradient of 5–20% methanol in ethyl acetate. Elution with 5% methanol in ethyl acetate afforded triphenyl phosphine. Elution with 8% methanol in ethyl acetate afforded a 2:1 mixture of exo:endo-3-acetyl-1-azabicyclo[2.2.1]heptane (1.15 g, 0.0082 moles). Elution with 15% methanol in ethyl acetate afforded the title compound (D38) (1.9 g, 0.0047 moles, 23%).

m.p. 228°–230° C.

$^1$H NMR (CDCl$_3$), 270 MHz, δ: 1.1–1.2 (1H, m, 5-H), 1.5–1.64 (1H, m, 5-H), 2.2–2.31 (2H, m), 2.5–2.65 (1H, m), 2.65–2.86 (4H, m), 3.03–3.14 (1H, m), 3.67 (1H, d, J=26Hz, CH=P), 7.36–7.7 (15H, m, Ar).

$^{13}$C NMR (CDCl$_3$) 67 MHz δ: 30.6 (C-5), 42.1 (C-4), 50.15 (d, J=108Hz, CH=P), 52.4 (d, J=13Hz, C-3), 54.0, 58.9, 60.0 (C-2,6,7), 127.3 (d, J=90Hz), 128 (d, J=12Hz), 131 (d, J=3Hz), 133.0 (d, J=0.4Hz), 194 (d, J=2Hz).

Elution with 20% methanol in ethyl acetate afforded the title compound (D39) (0.9 g, 0.0022 mole, 11%) m.p. 215°–217° C.

$^1$H NMR (CDCl$_3$), 270 MHz, δ: 1.3–1.45 (1H, m, 5-H), 1.6–1.72 (1H, m, 5-H), 2.35–2.43 (1H, m), 2.5–3.0 (7H, m), 3.73 (1H, d, J=26Hz, C$\underline{H}$=P), 7.4–7.7 (15H, m, Ar).

$^{13}$C NMR (CDCl$_3$), 67 MHz, δ: 25.1 (C-5), 42.9 (C-4), 51.6 (d, J=108Hz, C=P), 51.8 (d, J=14Hz, C-3), 54.3, 56.2 (d, J=2.6Hz), 62.0 (C-2,6,7), 127.4 (d, J=90Hz), 128.8 (d, J=12.5Hz), 131.9 (d, J=2.6Hz), 133 (d, J=10.4Hz), 192.2 (d, J=2Hz, C=O).

DESCRIPTION 40

(±)
exo-3-(1-m-Nitrobenzoyl-1,2,3-triazol-4-yl)-1-azabicyclo(2.2.1)heptane (D40)

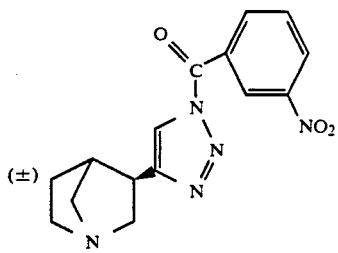

(D40)

A solution of (±) exo-3-(triphenylphosphinemethylenecarbonyl)-1-azabicyclo[2.2.1]heptane (D39) (0.9 g, 0.0026 mole) in acetonitrile (50 ml) was treated with metanitrobenzoyl azide (1 g, 0.0052 mole) and heated under reflux for 1 h. The solution was then concentrated in vacuo to a gum which was dissolved in chloroform/ethyl acetate 1:10 (10 ml) and held at 0° C. for 3 days when the title compound (D40) crystallised (320mg, 0.001 mole, 37%) m.p. 168°-172° C. (dec).

$^1$H NMR, (DMSO) 250 MHz δ: 1.6-1.75 (1H, m, 5-H), 1.85-2.0 (1H, m, 5-H), 2.7-3.05 (8H, m), 7.65 (1H, t, J=7Hz), 7.85 (1H, s, CH=C), 8.3 (2H, t, J=7Hz), 8.65 (1H, s).

$^{13}$C NMR (DMSO) 67 MHz δ: 27.9 (C-5), 37.3 (C-4), 42.4 (C-3), 51.7, 56.9, 58.3 (C-2,6,7), 123.7, 125.0, 129.7 and 135.6 (CH-Ar), 125 (CH-triazole), 129.6 (C-triazole), 147.4 and 147.8 (C-Ar), 167.8 (C=O).

DESCRIPTION 41

(±)
exo-3-(2H-1,2,3-Triazol-4-yl)-1-azabicyclo[2.2.1]heptane (D41)

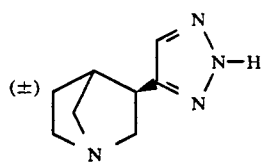

(D41)

A solution of (±) exo-3-(1-metanitrobenzoyl-1,2,3-triazol-4-yl)-1-azabicyclo[2.2.1]heptane (D40) (450 mg, 0.00143 mole) in methanol (50 ml) was heated under reflux for 24 h and then concentrated to a gum. Chromatography on basic alumina in a gradient of 5-40% methanol in chloroform afforded the title compound (D41) (130mg) which crystallised as needles from ethyl acetate. m.p. 155°-160° C.

$^1$H NMR (CD$_3$OD) δ: 1.4-1.5 (1H, m), 1.7-1.85 (1H, m), 2.45 (1H, d, J=8Hz), 2.6-3.15 (7H, m), 7.65 (1H, s).

$^{13}$C NMR (CD$_3$OD) δ: 30.7 (C-5), 39.9 and 44.6 (C-3,4), 49.9, 54.2, 58.6 (C-2,6,7), 128.3 (ArCH), 149.7 (ArC).

DESCRIPTION 42

(±)
endo-3-(2H-1,2,3-Triazol-4-yl)-1-azabicyclo-[2.2.1]heptane (D42)

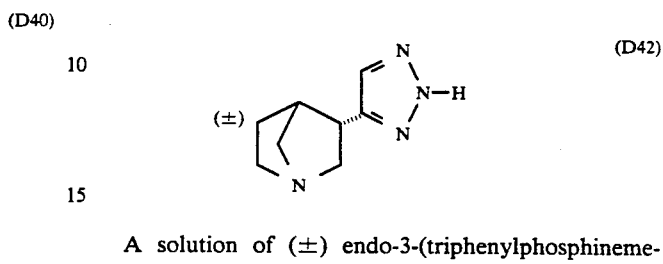

(D42)

A solution of (±) endo-3-(triphenylphosphinemethylenecarbonyl)-1-azabicyclo[2.2.1]heptane (D38) (0.4 g, 0.001 mole) was dissolved in acetonitrile (30 ml) and treated with metanitrobenzoylazide (0.39 g, 0.002 mole) under nitrogen at reflux for 1 h. The solution was then concentrated in vacuo to a gum which was chromatographed on basic alumina in a gradient of 4-15% methanol in chloroform. The title compound (D42) (0.11 g, 67%) which had been deprotected on the column crystallised from methanol/ether as needles m.pt. 145°-147° C.

$^1$H NMR (CDCl$_3$) δ: 1.18-2.4 and 2.4-2.58 each (1H, m, 5-H), 2.6-2.75 (2H, m), 2.75-3.05 (4H, m), 3.3-3.52 (2H, m), 7.48 (1H, s), 8.73 (1H, m).

$^{13}$C NMR (CDCl$_3$) δ: 24.0 (C-5), 37.8 and 42.4 (C-3,4), 54.0, 58.3 and 61.1 (C-2,6,7) 131.1 (C-5,) and 146.8 (C-4').

DESCRIPTION 43

(±)
exo-3-(2H-Tetrazol-5-yl)-1-azabicyclo[2.2.1]heptane (D43)

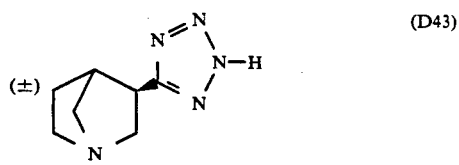

(D43)

(±) exo 3-Cyano-1-azabicyclo[2.2.1]heptane (D19) (1.63 g; 0.013 mole) in dry tetrahydrofuran (10 ml) was treated with azido trimethylsilane (5.3 ml, 0.04 mole) in an autoclave at 110° C. for 16 h. The reaction mixture was dissolved in methanol and crystallised from methanol/ethyl acetate to afford the title compound (D43) (1.65 g, 0.01 mole, 76%) m.p. >250° C.

$^1$H NMR (DMSO) δ: 1.5-1.65 (1H, m, 5-H), 1.75-1.93 (1H, m, 5-H), 2.65-3.45 (8H, m), 4.5 (1H, Br s, NH).

$^{13}$C NMR (DMSO) δ: 28.8 (C-5), 38.6 and 42.8 (C-3, C-4), 52.9, 57.6 and 60.0 (C-2, C-6, C-7), 162.8 (C-5').

EXAMPLE 1

(±) 5-(2-Methyl-1.2.3-triazole-4-yl)-1-azabicyclo-[3.2.1]octane (E1)

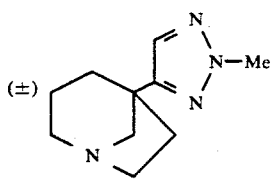

A solution of 5-ethynyl-1-azabicyclo[3.2.1]octane (D6) (1 g, 0.0074 mol) in tetrahydrofuran (5 ml) was treated with azidotrimethylsilane (1.27 g, 0.011 mol) at 140° C. for 8 h in a PTFE lined autoclave. The reaction was then cooled and treated with methanol (30 ml). The solution was then concentrated in vacuo to a brown gum. The gum was then taken up in methanol (30 ml) and treated with diazomethane in ether (excess) and allowed to stand for 15 min at 20° C. The reaction mixture was then concentrated in vacuo to a gum and chromatographed on neutral alumina in a gradient of 10–40% methanol in ethyl acetate. Elution with 15% methanol in ethyl acetate afforded the required product as a gum which slowly crystallised on standing. Recrystallisation from petrol afforded the title compound (E1, 99mg, 7%) as needles.

m.p. 65°–70° C.

$^1$H NMR (CDCl$_3$) δ: 1.4–1.55 (1H, m), 1.7–2.05 (5H, m), 2.7–3.2 (6H, m), 4.1 (3H, s, NCH$_3$), 7.3 (1H, s, CH).

$^{13}$C NMR (CDCl$_3$) δ: 19.8 (C-4), 36.5 and 37.0 (C3 and 6), 41.5 (CH$_3$), 52.2, 54.4 and 65.5 (C, 2, 7 and 8), 130.9 (C4′) and 153.4 (C5′).

ALTERNATIVE SYNTHESIS

Example 1

(±) 5-(2-Methyl-1,2,3-triazol-4-yl)-1-azabicyclo-[3.2.1]octane (E1)

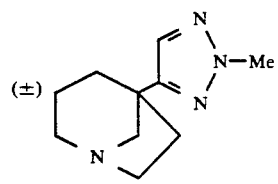

A solution of (±)-5-(2H-1,2,3-triazol-4-yl)-1-azabicyclo[3.2.1]octane (D33) (0.5 g, 0.0028 mole) in methanol (20 ml) was treated at 0° C. with excess diazomethane in ether for 2 h. The solution was then concentrated in vacuo to a gum which was chromatographed on alumina in a gradient of 4–20% methanol in ethyl acetate. The second fraction eluting in 12% methanol in ethyl acetate afforded the title compound (E1) (120mg) identical by NMR, TLC, mpt to the compound described previously.

Example 2

(±) 3-(2-Methyltetrazol-5-yl)-1-azabicyclo[2.2.2]octane oxalate salt (E2)

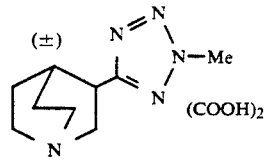

(±) 3-Cyano-1-azabicyclo[2.2.2]octane (EP-A-0 261 763, Description 1) (0.56 g, 4.1 mmol) was dissolved in dry tetrahydrofuran (1 ml) and the solution placed in a PTFE lined autoclave. Azidotrimethylsilane (1.66 ml, 6.6 mmol) was added and the mixture heated to 130° C. for 5 h. The resulting mixture was transferred to a flask using methanol, excess solvent removed under reduced pressure and an ethereal solution of diazomethane (10 mmol) was added at 0° C. The mixture was stirred for 2 h and then evaporated to dryness under reduced pressure. The resulting oil was purified by column chromatography using neutral alumina and eluting with 10% methanol/ethyl acetate. $^1$H nmr indicated the mixture contained a 4:1 ratio of 2-methyl isomer to 1-methyl isomer and this mixture (100mg, 13%) was crystallised as the oxalate salt and recrystallised from methanol/diethyl ether. The oxalate salt also contained 20% of the N 1-methyl isomer.

$^1$H NMR (oxalate) (d$_6$-DMSO) δ: 1.87 (2H, m), 2.10 (2H, m), 2.42, 2.59 together (1H, m), 3.34 (4H, m), 3.76 (3H, complex m), 4.12, 4.46 (1:4) together (3H, s, N-Me), 6.45 (bs, oxalate).

Major Isomer $^{13}$C NMR (oxalate) (d$_6$-DMSO) δ: 18.3 and 22.8 (C5 and C7), 24.7 and 30.5 (C3 and C4), 39.6 (CH$_3$), 45.16, 45.5, 48.7 (C2, C6, C8), 164.7 oxalate, 166.0, C5′.

Analysis: C$_9$H$_{15}$N$_5$.C$_2$H$_2$O$_4$ requires C, 46.64; H, 6.05; N, 24.72. Observed C, 46.53; H, 6.14; N, 24.28.

MS: M$^+$=193 (C$_9$H$_{15}$N$_5$).

Example 3

(±) 5-(2-Methyltetrazol-5-yl)-1-azabicyclo[3.2.1]octane oxalate salt (E3)

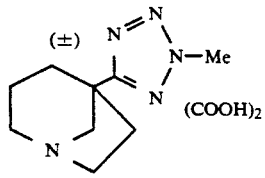

To 1-azabicyclo[3.2.1]oct-5-ylcarbonitrile (EP-A-0 287 356, Description 21) (1 g, 0.007 mol) in dioxan (3 ml) was added azidotrimethylsilane (2.4 ml, 0.018 mol, 2.6 eq). The mixture was heated at 130° C. in a PTFE lined autoclave for 5 h. The cooled reaction mixture was dissolved in methanol, then evaporated to dryness to remove any hydrazoic acid. The residue was re-dissolved in methanol and treated with an excess of diazomethane in ether, i.e. until the yellow colour persisted. The reaction was stirred at room temperature for 15 min then concentrated in vacuo to afford a brown oil. The ether-soluble component was chromatographed on alumina in 5% methanol in ethyl acetate. The first fraction contained unreacted starting material. The second fraction contained the title compound free base as a colourless oil (96 mg, 0.497 mmol, 7% yield). This compound was crystallized as the oxalate salt (E3), m.p. 126°-128° C.

¹H NMR (CD₃OD) oxalate salt δ: 1.98-2.3 (6H, m), 3.37-3.5 (2H, m), 3.53-3.68 (2H, m), 3.7-3.85 (2H, m), 4.35 (3H, s, CH₃).

¹³C NMR (CD₃OD) oxalate salt δ: 18, 33.7, 34.9 together (C-3, C-4, C-8), 40.2 (CH₃), 43.2 (C-5), 52, 53.9 and 61.9 together (C-2, C-6, C-7), 166.7 (oxalate), 168.8 (C5').

A third fraction of 54 mg eluted as a mixture of N-1 and N-2 methyl tetrazoles. NMR of the mixture indicated that the N-1 methyl isomer represented 9% of the total yield of tetrazole.

Examples 4 and 5

(±)
exo-3-(2-Methyltetrazol-5-yl)-1-azabicyclo-[2.2.1]heptane hydrochloride salt (E4)

(±)
exo-3-(1-Methyltetrazol-5-yl)-1-azabicyclo-[2.2.1]heptane oxalate salt (E5)

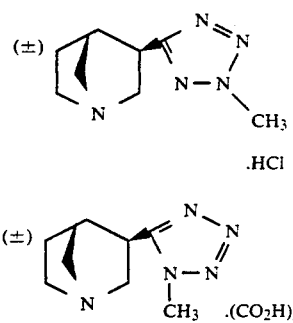

(±) exo-3-Cyano-1-azabicyclo[2.2.1]heptane (D 19) (515 mg, 4.22 mmol) was dissolved in dry tetrahydrofuran (5 ml), azidotrimethylsilane (2.0 ml, 1.74 g, 15.1 mmol) was added and the mixture placed in a PTFE lined autoclave. The solution was then heated to 110° C. for 20 h, and the resulting mixture was transferred to a flask using methanol. Excess solvent was removed under reduced pressure, and ethereal solution of diazomethane (10 mmol) was added at 0° C. The mixture was stirred for 1.5 h, then evaporated to dryness under reduced pressure, and the residue dissolved in saturated aqueous potassium carbonate solution. The aqueous solution was extracted with ethyl acetate (2×250 ml), the organic extracts dried (Na₂SO₄) filtered and evaporated to dryness under reduced pressure. The residue was purified by column chromatography using neutral alumina and eluting with EtOAc/MeOH 2%. The faster running fraction was crystallised from diethyl ether as the hydrochloride salt, and recrystallised from methanol, acetone and diethyl ether to yield the title compound (E4) as a white crystalline solid (143 mg) m.p. 185°-187° C.

¹H nmr (d₆ DMSO, 270 MHz) 1.86 (1H, m), 2.06 (1H, m), 3.05 (1H, d), 3.20 (2H, m), 3.33 (2H, m), 3.58 (2H, m), 3.76 (1H, m), 4.33 (3H, s, tetrazole Me).

¹³C nmr (d₆ DMSO, 67 MHz) 26.51, 36.36, 41.13, 51.23, 56.42, 56.79, 166.12 (quart-C).

MS: C₈H₁₃N₅ requires 179.1161 observed 179.1173

Analysis

C₈H₁₃N₅ 0.7HCl.H₂O % required C, 43.14; H, 7.05, N, 31.45. % found C, 43.20; H, 7.19; N, 31.60.

The slower-running isomer (E5) was crystallised and recrystallised from methanol/diethyl ether as the oxalate salt (32 mg) m.p. 124°-127° C.

¹H nmr (d₆ DMSO, 270 MHz) 1.86 (1H, m), 2.03 (1H, m), 3.06 (1H, d), 3.25 (4H, complex m), 3.62 (3H, m), 4.03 (3H, s, tetrazole-Me).

¹³C nmr (d₆ DMSO, 67 MHz), 26.75, 33.35, 34.06, 40.42, 51.53, 56.75, 56.95, 155.73, 163.95 (quart-C, tetrazole).

MS: C₈H₁₃N₅ requires 179.1161. observed 179.1173.

Examples 6 and 7

(±)
endo-3-(2-Methyltetrazol-5-yl)-1-azabicyclo-[2.2.1]heptane hydrochloride salt (E6) and (±)
endo-3-(1-Methyltetrazol-5-yl)-1-azabicyclo-[2.2.11 heptane oxalate salt (E7)

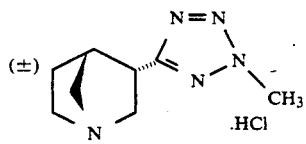

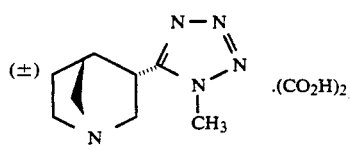

(±) endo-3-Cyano-1-azabicyclo[2.2.1]heptane (D20) (622 mg, 5.1 mmol) was used in the same was as described in Examples 4 and 5. The purification was performed in an identical manner, and the faster running isomer was crystallised from diethyl ether as the hydrochloride salt, and recrystallised from acetone, diethyl ether to afford the title compound (E6) as a white crystalline solid (76 mg) m.p. 197°-200° C.

¹H nmr (d₆ DMSO, 270 MHz) 1.42 (1H, m), 1.84 (1H, m), 3.19 (2H, m), 3.40 (4H, complex m), 3.81 (1H, dt), 4.01 (1H, m), 4.36 (3H, s, tetrazole Me). ¹³C nmr (d₆ DMSO, 67 MHz) 21.92, 35.09, 35.10, 40.01, 51.91, 54.49, 59.18, 163.92.

MS: C₈H₁₃N₅ requires 179.1161 observed 179.1173.

Analysis

C₈H₁₃N₅.HCl
% required: C, 44.55; H, 6.50; N, 32.48. % found: C, 44.52; H, 6.41; N, 32.86.

The slower running isomer contaminated with 5% of the faster running isomer was crystallised and recrystallised from methanol, diethyl ether as the oxalate salt to afford the title compound (E7) as a white crystalline solid (15 mg), m.p. 183°-185° C.

¹H nmr (d₆ DMSO, 270 MHz) 1.32 (1H, m), 1.78 (1H, m), 3.29 (5H, complex m), 3.54 (1H, m), 3.73 (1H, dt), 4.00 (1H, m), 4.05 (2.85H, s, tetrazole-1-Me), 4.35 (0.15H, tetrazole-2-Me).

¹³C nmr (d₆ DMSO, 67 MHz) 22.32, 33.34, 33.45, 52.22, 55.36, 59.75, 153.89 (oxalate), 164.15 (quart-C tetrazole).

Example 8

4-(2-Methyltetrazol-5-yl)-1-azabicyclo2.2.1] heptane oxalate salt (E8)

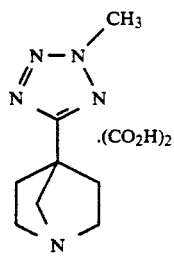

1-Azabicyclo[2.2.1]hept-4-yl carbonitrile (D15, 1 g, 0.008 mole) in dry tetrahydrofuran (2 ml) was treated with azidotrimethylsilane (3.18 ml, 0.024 mole) and heated in an autoclave at 110° C. for 17 h. The reaction was then dissolved in methanol (50 ml) and then concentrated in vacuo to remove any hydrazoic acid. The residue was redissolved in methanol (20 ml) cooled to 0° C. and treated with excess diazomethane in ether until the yellow colour of the diazomethane persisted. After 30 min at 0° C. the solution was concentrated in vacuo to a gum which was chromatographed on alumina in a gradient of ethyl acetate to 10% methanol in ethyl acetate. Elution with ethyl acetate afforded unchanged nitrile. Elution with 2% methanol in ethyl acetate afforded the N-2 methylated isomer as a pale yellow oil (280 mg). The title compound (E8) crystallised as the oxalate salt from methanol/ether as cubes (0.36 mg, 0.0014 mole, 17%) m.p. 139°–144° C.

$^1$H NMR (CD$_3$OD) δ: 2.23–2.37 (2H, m, 3-H, 5-H), 2.46–2.64 (2H, m, 3-H, 5-H), 3.4–3.58 (2H, m, 2-H, 6-H), 3.62 (2H, s, 7-CH$_2$), 3.67–3.8 (2H, m, 2-H, 6-H), 4.38 (3H, s, CH$_3$).

Example 9

(±) 3-(2-Ethyltetrazol-5-yl)-1-azabicyclo[2.2.2]octane oxalate salt (E9)

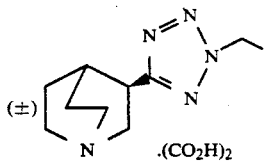

This compound was prepared from (±) 3-cyano-1-azabicyclo[2.2.2]octane (EP-A-0 261 763, Description 1) in a similar manner to the compound of Example 2 using an ethereal solution of diazoethane prepared from N-nitroso-N-ethyl urea[1,2]. The resulting oil was purified by column chromatography using neutral alumina and eluting with 2% MeOH/EtOAc. $^1$H NMR indicated that the mixture contained a 12:1 ratio of the 2-ethyl isomer to 1-ethyl isomer and this mixture (100 mg, 17%) was crystallised and the title compound E9 recrystallised from methanol/diethyl ether as the oxalate salt (containing 8% of the 1-ethyl isomer).

1. F. Arndt, 'Organic Syntheses', Coll.Vol.II, John Wiley and Sons, New York, 1943, p461.
2. J. Werner, J. Chem. Soc., 1093 (1919).

$^1$H NMR (d$_6$ DMSO, 270 MHz): 1.43 (0.24H, t, CH$_3$ of 1-ethyl isomer), 1.50 (2.76H, t, CH$_3$ of 2-ethyl isomer), 1.68 (2H, bm), 1.98 (2H, bm), 2.34 (1H, m), 3.28 (4H, m), 3.66 (3H, complex m), 4.39 (0.16H, q, CH$_3$C$\underline{H}_2$ of 1-ethyl isomer), 4.67 (1.84H, q, CH$_3$C$\underline{H}_2$ of 2-ethyl isomer).

$^{13}$C NMR (d$_6$ DMSO, 67 MHz) 14.18 (CH$_3$), 18.36 (CH$_2$), 22.81 (CH$_2$), 24.77 (CH), 30.61 (CH), 45.19 (CH$_2$), 45.54 (CH$_2$), 48.09 (CH$_2$), 48.79 (CH$_2$), 164.66 (quart-C), 165.98 (quart-C).

MS C$_{10}$H$_{17}$N$_5$ requires 207.
M+ observed 207.

Analysis

C$_{10}$H$_{17}$N$_5$.C$_2$H$_2$O$_4$.½H$_2$O % required: C, 47.06; H, 6.54; N, 22.88. % found: C, 47.36; H, 6.20; N, 22.68.

Example 10

4-(2-Methyl-1,2,3-triazol-4-yl)-1-azabicyclo[2.2.1]-heptane oxalate salt (E10)

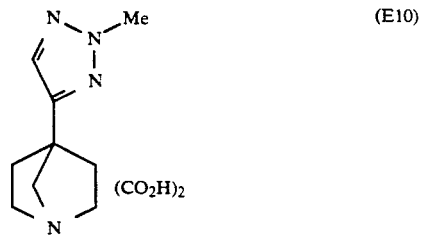

4-(2H-1,2,3-triazole-4-yl)-1-azabicyclo[2.2.1]heptane (D26) (400 mg, 0.0024 moles) was dissolved in methanol (20 ml) and treated with excess diazomethane in ether at 0° C. for 2 h when the triazole was completely methylated. The solution was then concentrated in vacuo to a gum which was chromatographed on alumina in a gradient of 4–15% methanol in ethyl acetate. Elution with 12% methanol in ethyl acetate afforded the title compound (E10) (150 mg, 0.00084 mole, 35%). The oxalate salt crystallised from methanol/ether as needles.

M.p 130°–135° C.

$^1$H NMR (CD$_3$OD) 270 MHz δ: 2.13–2.27 (2H, m, 3,5-H), 2.35–2.5 (2H, m, 3,5-H), 3.38–3.55 (4H, m), 3.6–3.75 (2H, m, 2,6-H), 4.17 (3H, s, CH$_3$), 7.7 (1H, s, CH=N).

$^{13}$C NMR (CD$_3$OD) 67 MHz δ: 34.0 (C-3,5), 41.9 (CH$_3$), 46.2 (C-4), 54.4 (C-2,6), 62.8 (C-7), 133.2 (CH=N), 146.2 (C=), 166.8 (CO$_2$H)$_2$.

Example 11, Example 12, Example 13

(±) 3-(2-Methyl-1,2,3-triazol-4-yl)-1-azabicyclo [2.2.2]octane oxalate salt (E11)

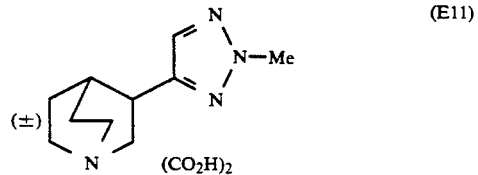

(±) 3-(1-Methyl-1,2,3-triazol-4-yl)-1-azabicyclo-[2.2.2]octane oxalate salt (E12)

-continued

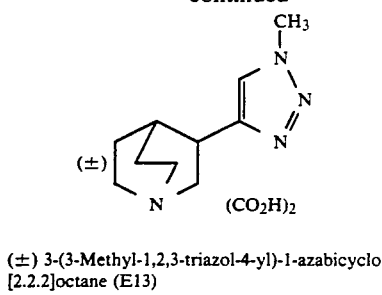

(±) 3-(3-Methyl-1,2,3-triazol-4-yl)-1-azabicyclo[2.2.2]octane (E13)

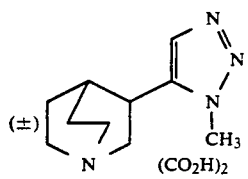

A solution of (±)3-(2H-1,2,3-triazol-4-yl)-1-azabicyclo[2.2.2]octane (D30) (1 g, 0.0056 mole) in methanol was treated with diazomethane in ether at 0° C. until a faint yellow colour persisted. The solution was allowed to warm to room temperature and then concentrated in vacuo to a gum. The solution was then chromatographed on alumina in a gradient of 3–15% methanol in ethyl acetate. Elution with 10% methanol in ethyl acetate afforded a fraction containing two N-methyl isomers (0.31 g). Crystallisation from ether/petrol afforded the title compound (E13) as needles (25 mg) mpt 126°–129° C.

$^1$H NMR (CDCl$_3$) δ: 1.3–1.45 (1H, m), 1.51–1.63 (1H, m), 1.63–1.75 (2H, m), 1.78–1.85 (1H, m), 2.75–3.0 (6H, m), 3.25–3.45 (1H, m), 3.9 (3H, s), 7.5 (1H, s).

$^{13}$C NMR CDCl$_3$ δ: 21, 25.5, 27.3, 32.0, 34.5, 47, 47.9, 53.5, 131.1, 140.

The mother liquors were treated with oxalic acid in methanol until no further precipitate was produced. Crystallisation from acetone/methanol afforded the title compound (E11) (79 mg) as needles m.p. 127°–132° C.

$^1$H NMR (CD$_3$OD) (oxalate salt) δ: 1.73–1.97 (2H, m), 2.05–2.2 (2H, m), 2.25–2.34 (1H, m), 3.33–3.78 (7H, m), 4.15 (3H, s), 7.6 (1H, s).

$^{13}$C NMR (CD$_3$OD) (oxalate salt) δ: 19.3 and 24.3 (C-5,8), 27.2, 32.2 and 41.9 (CH$_3$, C-3, C-4), 47.3, 47.8 and 51.6 (C-2,6,7), 133.6 (Ar—CH), 149.0 (Ar—C), 165.4 (CO$_2$H)$_2$.

Elution with 15% methanol in ethyl acetate afforded a second fraction. Treatment with excess oxalic acid in methanol afforded the title compound (E12) (30 mg) which crystallised from acetone as needles.

m.p. 97°–102° C.

$^1$H NMR (CD$_3$OD) oxalate δ: 1.78–2.0 (2H, m), 2.08–2.22 (2H, m), 2.26–2.35 (1H, m), 3.35–3.84 (7H, m), 4.13 (3H, s, CH$_3$), 7.95 (1H, s).

$^{13}$C NMR (CD$_3$OD) oxalate δ: 19.4 and 24.4 (C-5,8), 27.4, 32.3 and 37.1 (C-3,4 and CH$_3$), 47.3, 47.7 and 51.6 (C-2,6,7), 124.8, (C-5'), 148.5 (C-4') and 167.7 (CO$_2$H)$_2$.

Example 14

(±) exo-3-(2-Methyl-1,2,3-triazol-4-yl)-1-azabicyclo[2.2.1]heptane oxalate salt (E14)

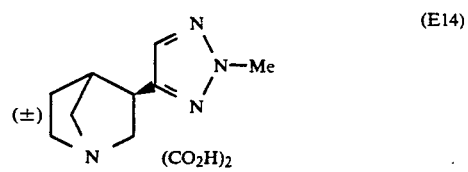

A solution of (±) exo-3-(2H-1,2,3-triazol-4-yl)-1-azabicyclo[2.2.1]heptane (D41) (450 mg, 0.0014 mole) in methanol (50 ml) was treated with excess diazomethane in ether at 0° C. The solution was allowed to warm to room temperature over 1 h and then concentrated in vacuo to a gum. Chromatography on alumina in a gradient of 5–40% methanol in ethyl acetate afforded two main fractions. Fraction 1 eluted in a gradient of 15–20% methanol in ethyl acetate and consisted of two N-methyl isomers. The oxalate salt of the major isomer (E14) (60 mg) crystallised from acetone/ether as needles.

m.p. 122°–125° C.

$^1$H NMR oxalate (CD$_3$OD) δ: 1.85–2.0 (1H, m), 2.1–2.3 (1H, m), 3.0 (1H, d, J=3Hz), 3.15–3.75 (7H, m), 4.13 (3H, s, CH$_3$), 7.6 (1H, s).

$^{13}$C NMR (oxalate) (CD$_3$OD) δ: 28.2 (C-5), 38.3 (CH$_3$), 43.8 (C-4), 49.3, 53.5, 58.5 (C-2,6,7), 133.4 (C-5'), 149.5 (C-4'), 166.8 (CO$_2$H)$_2$.

Example 15

(±) endo-3-(2-Methyl-1,2,3-triazol-4-yl)-1-azabicyclo[2.2.1]heptane oxalate salt (E151)

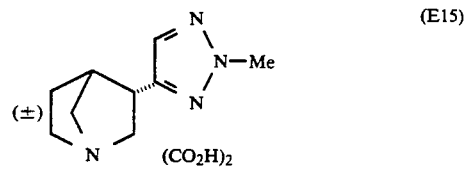

(±) endo-3-(2H-1,2,3-triazol-4-yl)-1-azabicyclo[2.2.1]heptane (D42) (300 mg, 0.0018 mole) in ethanol (10 ml) was treated with a solution of diazomethane in ether (0.01 mole in 10 ml) at 0° C. The solution was allowed to warm to room temperature over a period of 4 h. The reaction was then concentrated in vacuo to a gum which was chromatographed on alumina in a gradient of 4–40% methanol in ethyl acetate. The major fraction which eluted in 30% methanol in ethyl acetate was converted to the oxalate salt. Crystallisation from acetone/ether afforded the title compound (E15) (61 mg, 0.23 mole, 13%).

m.p. 63°–65° C.

$^1$H NMR (CDCl$_3$) δ: 1.13–1.25 and 1.25–1.43 each (1H, m, 5-H), 2.4–2.85 (6H, m), 3.1–3.3 (2H, m), 4.08 (3H, s), 7.28 (1H, s).

Example 16

4-(2-Ethyl-1,2,3-triazol-4-yl)-1-azabicyclo2.2.1]heptane oxalate salt (E16)

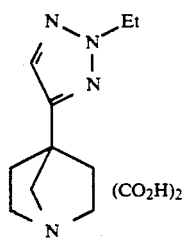

4-(2H-1,2,3-Triazol-4-yl)-1-azabicyclo[2.2.1]heptane (D26) (0.63 g, 3.8 mmole) in ethanol (40 ml) at 0° C. was treated with an excess of diazoethane prepared as described in Example 9 in ether until a faint yellow colour persisted on stirring. The reaction was concentrated in vacuo to afford a mixture containing the three possible N-ethylated isomers. Chromatography on fine neutral alumina in a gradient of 3–10% methanol in ethyl acetate afforded the major fraction (0.326 g, 0.0011 mole, 30%). The oxalate salt of this crystallised from acetone to afford the title compound (E16) m.p. 124°–126° C.

$^1$H NMR (d$_6$ DMSO) oxalate salt δ: 1.52 (3H, t, J=5.24 Hz), 2.09–2.21 (2H, m), 2.29–2.32 (2H, m), 3.38–3.50 (4H, m), 3.52–4.18 (2H, m), 4.50 (2H, q, J=5.24 Hz), 7.93 (1H, s).

$^{13}$C NMR (d$_6$ DMSO) oxalate salt δ: 14.95 (CH$_2$CH$_3$), 33.00 (C-3, C-5), 44.7 (C-4), 49.70 (C-7), 52.66 (C-2, C-6), 61.21 (CH$_2$CH$_3$), 132.43 (C-5'), 145.20 (C-4'), 164.90 (CO$_2$H)$_2$.

Example 17 exo-3-(2-Methyltetrazol-5-yl)-1-azabicyclo[3.2.1]octane oxalate salt (E17)

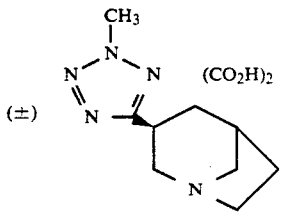

exo-3-Cyano-1-azabicyclo[3.2.1]octane (EP 0261763 Description 5, 2.3 g, 0.017 mole) was dissolved in a dry tetrahydrofuran (5 ml) and then treated with azidotrimethylsilane (3eq, 6.72 ml, 0.051 mole) and heated in an autoclave at 110° C. for 12 hours. After allowing to cool to room temperature the mixture was concentrated in vacuo to a gum. This crude intermediate was dissolved in a small quantity of methanol and treated portionwise with freshly prepared diazomethane (3eq) at 0° C. Stirring at 0° C. was continued for one hour after complete addition. The mixture was then concentrated in vacuo. The crude residue obtained was purified by trituration with ethyl acetate. This residue was then chromatographed on neutral alumina eluting with 5% MeOH/EtOAc. The colourless oil obtained was converted to the oxalate salt. Recrystallisation from an acetone/methanol mixture, afforded the title compound (E17) as colourless crystals (0.081 g, 5%) m.p. >250° C.

Oxalate Salt $^1$H NMR (D$_2$O) δ: 1.94–2.10 (1H, m), 2.10–2.30 (2H, m), 2.30–2.49 (1H, m) together (H-4, H-6), 2.90–3.00 (1H, m) (H-5), 3.38–3.58 (2H, m), 3.58–3.82 (4H, m), 3.82–4.00 (1H, m) together (H-2, H-3, H-7, H-8), 4.15 (3H, s).

$^{13}$C NMR (D$_2$O) δ: 27.32 (CH$_3$), 29.36 and 35.76 (C-4,6), 35.88 and 36.61 (C-3,5), 54.13, 56.80 and 61.49 (C-2,7,8), 157.86 (C-5'), 176.33 (CO$_2$H)$_2$.

EXAMPLE 18

(±) exo-3-(2-Ethyltetrazol-5-yl)-1-azabicyclo[2.2.1]heptane hydrochloride salt (E18)

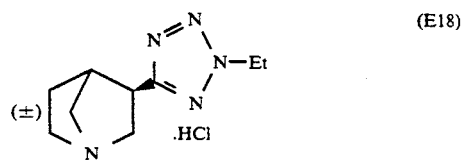

(±) exo-3-(2H-tetrazol-5-yl)-1-azabicyclo[2.2.1]heptane (D43) (0.5 g, 0.003 mole) in ethanol (10 ml) was cooled to 0° C. and treated with a solution of diazoethane in ether prepared from 4.4 g, 0.037 mole of N-nitroso-N-ethyl urea by the method of Arndt Eistert. The solution was allowed to warm to room temperature over a period of 4 h. The reaction was then concentrated in vacuo to a gum which was chromatographed on alumina in a gradient of 5–40% methanol in ethyl acetate. The major fraction eluted in 30% methanol in ethyl acetate to afford a gum which was distilled on a Kugelröhr b.p. 140°–150° C. at 0.1 mmHg. The hydrochloride salt crystallised from ether to afford the title compound (E18) (100 mg, 0.0004 mole, 15%) m.p. 43°–44° C.

$^1$H NMR (CD$_3$OD, 270 MHz) δ: 1.72 (3H, t, J=8Hz, CH$_3$), 2.06–2.18 and 2.28–2.44 each (1H, m, 5H), 3.3 (1H, d, J=3Hz), 3.46–4.0 (7H, m), 4.8 (2H, q, J=8Hz, CH$_2$CH$_3$).

$^{13}$C NMR (CD$_3$OD, 67 MHz) δ: 15.1, CH$_3$; 28.4, C-5; 38.9 and 43.6, C-3,4; 50.0, 54.1, 59.1 and 59.2, C-2,6,7 and CH$_2$CH$_3$; 167.8, C-5'.

Example 19

(±) exo-3-(2-Ethyl-1.2.3-triazol-4-yl)-1-azabicyclo[2.2.1]heptane oxalate salt (E19)

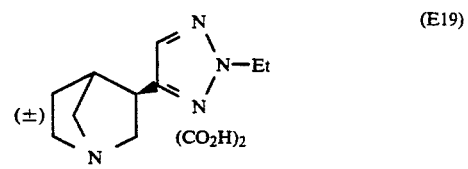

A solution of (±) exo-3-(2H-1,2,3-triazol-4-yl)-1-azabicyclo[2.2.1]heptane (D41) (300 mg, 0.0018 mole) in ethanol (10 ml) at 0° C. was treated with a solution of diazoethane in ether* prepared from 1.4 g, 0.012 mole of *Org. Syn. Coll. Vol II, 461 N-ethyl N-nitroso urea by the method of Arndt Eistert. The reaction was allowed to warm to room temperature over a period of 16 h. The reaction was then concentrated in vacuo to a gum which was chromatographed on alumina in a gradient of 5–40% methanol in ethyl acetate. The major component eluted in 20-30% methanol in ethyl acetate. The oxalate salt was prepared in the normal way to afford the title compound (D19) (0.340 g, 0.0012 mole, 66%) m.pt 128°-130° C.

*Org. Syn. Coll. Vol. II, 461.

$^1$H NMR (CDCl$_3$) (oxalate salt) δ: 1.2-1.35 and 1.6-1.75 each (1H, m, 5-H), 1.54 3H, t, J=8Hz), 2.35 (1H, d, J=9 Hz), 2.47-2.6 (1H, m), 2.6-3.03 (6H, m), 4.4 (2H, q, J=8Hz), 7.35 (1H, s, 5'-H).

$^{13}$C NMR (CDCl$_3$) (oxalate salt) δ: 14.8 (CH$_3$), 30.4 (C-5), 39.7 and 43.4 (C-3,4), 49.7, 53.9, 58.3 and 61.9 (C-2,6,7 and CH$_2$CH$_3$), 131.1 (C-5') and 151.3 (C-4').

C$_{12}$H$_{18}$N$_4$O$_4$ requires C, 51.0; H, 6.4; N, 19.8% found: C, 50.8; H, 6.4; N, 19.6%.

Example 20

(±) 3-[1-Methyl-1,2,4-triazol-3-yl]-1-azabicyclo[2.2.2]octane dihydrochloride salt (E20)

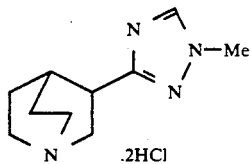

(E20)

(±) 3 Cyano-1-azabicyclo[2.2.2]octane (EP 0261763, Description 1, 1.0 g, 8.2 mmol) was dissolved in ethanol (5 ml) under nitrogen, cooled on ice to 0° C. and the solution saturated with HCl gas. The solution was allowed to warm to room temperature, stirred for 3 h and then evaporated to dryness under reduced pressure to yield the imidate hydrochloride as a white crystalline solid. This was dissolved in ethanol (20 ml) under nitrogen, and methylhydrazine (0.6 ml, 1.3 equivs) was added with dry triethylamine (2.86 ml, 2.5 equivs). The suspension was stirred at room temperature for 3 h, and evaporated to dryness under reduced pressure at a temperature not greater than 30° C. The resulting white solid was dissolved in neat formic acid (20 ml) and the yellow solution stirred for 30 min, and refluxed for 1.5 h. The cooled solution was then poured into aqueous saturated potassium carbonate solution (50 ml), and the solution was extracted with chloroform (4×250 ml). The organic extracts were dried (Na$_2$SO$_4$), filtered and evaporated to dryness under reduced pressure to yield a yellow oil. This was purified by column chromatography using basic alumina and eluting with EtOAc/MeOH 1-5%. The faster running isomer was identified as the free base of the title compound (E20) and this was crystallised from ether as the dihydrochloride salt (240 mg, 11%) m.p. 220°-222° C.

$^1$H NMR (d$_6$ DMSO, 270 MHz) 1.74 (2H, m), 2.04 (2H, m), 2.41 (1H, pentet), 3.28 (4H, m), 3.62 (3H, m), 3.96 (3H, s, Me-azole), 8.84 (1H, s, CH-azole).

$^{13}$C NMR (d$_6$ DMSO, 67 MHz) 18.3 (CH$_2$), 22.7 (CH$_2$), 24.8 (CH$_3$), 32.3 (CH), 36.2 (CH), 45.0 (CH$_2$), 45.4 (CH$_2$), 48.5 (CH$_2$), 144.9 (CH-azole), 161.7 (azole quart C).

MS C$_{10}$H$_{16}$N$_4$ found 192.1377. requires 192.1375.

Analysis

C$_{10}$H$_{16}$N$_4$.2HCl Found C: 4 .90; H: 6.73; N: 20.86%. required C: 45.29; H: 6.84; N: 21.13%.

Biological Activity

Radio ligand Binding

Cerebral cortex from Hooded Lister rats (Olac, UK) is homogenised in 2.5 vols ice-cold 50 mM tris buffer pH 7.7 (at 25° C.). After centrifugation at 25,000×g at 4° C. for 15 min the pellet is resuspended in 2.5 vols buffer and the wash repeated 3 times more. The final resuspension is in 2.5 volumes and the homogenates are stored in 1 ml aliquots at −20° C.

Incubations (total volume 2 ml) are prepared using the above buffer with the addition of 2 mM magnesium chloride in the 3H-Oxotremorine-M (3H—OXO—M) experiments. For 3H-Quinuclidinyl Benzilate (3H—QNB), 1 ml of stored membranes is diluted to 30 ml and 0.1 ml mixed with test compound and 0.27 nM (c. 25,000 cpm) 3H—QNB (Amersham International). For 3H—OXO—M, 1 ml of membranes is diluted to 6 ml and 0.1 ml mixed with test compound and 2 nM (c. 250,000 cpm) 3H—OXO−M (New England Nuclear).

Non-specific binding of 3H—QNB is defined using 1 μM Atropine sulphate (2 μM Atropine) and of 3H—OXO—M using 10 μM Oxotremorine. Non-specific binding values typically are 5% and 25% of total binding, respectively. Incubations are carried out at 37° C. for 30 min and the samples filtered using Whatman GF/B filters. (In the 3H—OXO experiments the filters are presoaked for 30 min in 0.05% polyethylenimine in water). Filters are washed with 3×4 ml ice-cold buffer. Radioactivity is assessed using a Packard BPLD scintillation counter, 3 ml Pico-Fluor 30 (Packard) as scintillant.

This test provides an indication of the muscarinic binding activity of the test compound. The results are obtained as IC$_{50}$ values (i.e. the concentration which inhibits binding of the ligand by 50%) for the displacement of the muscarinic agonist 3H—OXO—M and the muscarinic antagonist 3H—QNB. The ratio IC$_{50}$(-3H—QNB)/IC$_{50}$(3H—OXO—M) gives an indication of the agonist character of the compound. Agonists typically exhibit a large ratio; antagonists typically exhibit a ratio near to unity.

The results are shown in Table 1:

TABLE 1

| Example No | [$^3$H] Oxo-M IC$_{50}$ (nM) | [$^3$H]-QNB IC$_{50}$ (nM) |
| --- | --- | --- |
| E1 | 14.2 | 3,000 |
| E2+ | 230 | 5,700 |
| E3+ | 100 | 8,200 |
| E4++ | 11.5 | 3,700 |
| E5+ | 349 | 95,000 |
| E6++ | 324 | 40,000 |
| E8+ | 250 | 56,000 |
| E9+ | 1000 | 8,300 |
| E10+ | 32 | 20,000 |
| E11+ | 56 | 6,552 |
| E13 | 750 | 38,000 |
| E14+ | 5.6 | 5,700 |
| E15+ | 10.5 | 18,500 |
| E16+ | 440 | 15,800 |
| E18++ | 400 | 5,500 |
| E19+ | 540 | 2,200 |

+ oxalate salt
++ hydrochloride salt

We claim:
1. A compound of formula (I) or a pharmaceutically acceptable salt thereof:

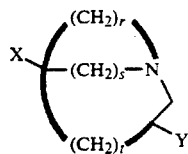
(I)

in which one of X and Y represents hydrogen and the other represents Z, where Z is a group

in which Q represents a 3-membered divalent residue completing a 5-membered aromatic ring and comprises two or three nitrogen atoms, any amino nitrogen being substituted by a $C_{1-2}$ alkyl, cyclopropyl or propargyl group, r represents an integer 2, s represents an integer of 1 or 2 and t represents 0, with the proviso that when Y is hydrogen s is 1.

2. A compound according to claim 1, in which (r,s,t) takes the value (2,1,0), or (2,2,0).

3. A compound according to claim 1, in which Z is 2-alkyl-1,2,3-triazol-4-yl, 2-alkyltetrazol-5-yl or 1-alkyl-1,2,4-triazol-3-yl in which 'alkyl' signifies a $C_{1-2}$alkyl, cyclopropyl or propargyl group.

4. A compound according to claim 3, in which Z is selected from 2-methyl-1,2,3-triazol-4-yl, 2-ethyl-1,2,3-triazol-4-yl, 1-methyl-1,2,4-triazol-3-yl, 2-methyltetrazol-5-yl and 2-ethyltetrazol-5-yl.

5.
(±) 3-(2-methyltetrazol-5-yl)-1-azabicyclo-[2.2.2]octane,
(±) exo-3-(2-methyltetrazol-5-yl)-1-azabicyclo-[2.2.1]heptane,
(±) exo-3-(1-methyltetrazol-5-yl)-1-azabicyclo-[2.2.1]heptane,
(±) endo-3-(2-methyltetrazol-5-yl)-1-azabicyclo-[2.2.1]heptane,
(±) endo-3-(1-methyltetrazol-5-yl)-1-azabicyclo-[2.2.1]heptane,
4-(2-methyltetrazol-5-yl)-1-azabicyclo[2.2.1]heptane,
(±) 3-(2-ethyltetrazol-5-yl)-1-azabicyclo[2.2.2]octane,
4-(2-methyl-1,2,3-triazol-4-yl)-1-azabicyclo[2.2.1]-heptane,
(±) 3-(2-methyl-1,2,3-triazol-4-yl)-1-azabicyclo-[2.2.2]octane,
(±) 3-(1-methyl-1,2,3-triazol-4-yl)-1-azabicyclo-[2.2.2]octane,
(±) 3-(3-methyl-1,2,3-triazol-4-yl)-1-azabicyclo-[2.2.2]octane,
(±) exo-3-(2-methyl-1,2,3-triazol-4-yl)-1-azabicyclo-[[2.2.1]heptane,
(±) endo-3-(2-Methyl-1,2,3-traizol-4-yl)-1-azabicyclo-[2.2.1]heptane,
4-(2-ethyl-1,2,3-triazol-4-yl)-1-azabicyclo[2.2.1]-heptane,
(±) exo-3-(2-ethyltetrazol-5-yl)-1-azabicyclo[2.2.1-heptane,
(±) exo-3-(2-ethyl-1,2,3-triazol-4-yl)-1-azabicyclo-[2.2.1]heptane or
3-[1-methyl-1,2,4-triazol-3-yl]-1-azabicyclo-[2.2.2]octane, or a pharmaceutically acceptable salt of any of the foregoing compounds.

6. A compound of formula (VIII) or a salt thereof:

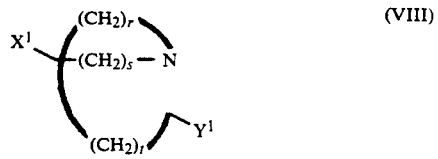
(VIII)

in which r is 2, s is 1 or 2, and t is 0, one of $X^1$ and $Y^1$ represents hydrogen and the other represents Z'', where Z'' is a group:

in which Q' represents 3-membered divalent residue completing a 5-membered aromatic ring and comprises two or three nitrogen atoms no amino nitrogen, if such is present in the ring, is substituted, with the proviso that when $Y^1$ is hydrogen then s is 1.

7. 4-(2H-1,2,3-Triazol-4-yl)-1-azabicyclo[2.2.1]-heptane,
(±) 3-(2H-1,2,3-Triazol-4-yl)-1-azabicyclo[2.2.2]-octane,
(±)exo-3-(2H-1,2,3-Triazol-4-yl)-1-azabicyclo[2.2.1]-heptane,
(±)endo-3-(2H-1,2,3-Triazol-4-yl)-1-azabicyclo[2.2.1]-heptane or
(±)exo-3-(2H-Tetrazol-5-yl)-1-azabicyclo[2.2.1]heptane.

8. A pharmaceutical composition for the treatment and/or prophylaxis of dementia which comprises an effective amount of a compound according to claim 1 and a pharmaceutically acceptable carrier.

9. A method of treatment and/or prophylaxis of dementia in mammals, which comprises administering to the sufferer an effective amount of a compound according to claim 1.

* * * * *